United States Patent [19]

von Bebenburg et al.

[11] 4,207,322
[45] Jun. 10, 1980

[54] 6-ARYL-S-TRIAZOLO-(4,3-ALPHA)-PYRIDO-(2,3-F)-(1,4)-DIAZEPINES

[75] Inventors: Walter von Bebenburg, Buchschlag; Norbert Schulmeyer, Mörfelden; Vladimir Jakovlev, Maintal, all of Fed. Rep. of Germany

[73] Assignee: Deutsche Gold und Silber-Scheideanstalt Vormals Roessler, Frankfurt, Fed. Rep. of Germany

[21] Appl. No.: 926,327

[22] Filed: Jul. 20, 1978

Related U.S. Application Data

[62] Division of Ser. No. 735,894, Oct. 26, 1976, Pat. No. 4,110,455.

[30] Foreign Application Priority Data

Nov. 4, 1975 [AT] Austria ................................. 8372/75

[51] Int. Cl.$^2$ ..................... A61K 31/44; C07D 471/14
[52] U.S. Cl. ........................................ 424/256; 546/82; 546/118
[58] Field of Search ........................... 546/82; 424/256

[56] References Cited

U.S. PATENT DOCUMENTS 4,073,792  2/1978  von Bebenburg et al. ...  260/239.3 B

FOREIGN PATENT DOCUMENTS 2416608  10/1974  Fed. Rep. of Germany ............. 546/82

Primary Examiner—Henry R. Jiles
Assistant Examiner—Natalia Harkaway
Attorney, Agent, or Firm—Cushman, Darby & Cushman

[57] ABSTRACT

There are produced 6-aryl-s-triazolo-(4,3-a)-pyrido-(2,3-f)-(1,4)-diazepines of the formula:

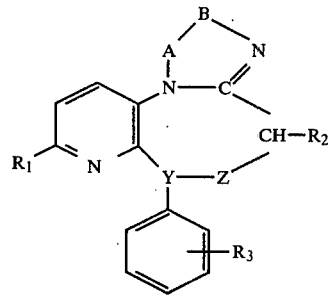

wherein $R_1$ is hydrogen, a halogen atom, an alkyl mercapto group having 1 to 6 carbon atoms, $R_2$ is hydrogen, an alkyl group with 1 to 6 carbon atoms, $R_3$ is hydrogen or a halogen or a halogen atom the structural part A–B is the group —CH$_2$=NH— and Y-Z is the group >C=N—, >C=N(→O), and Y-Z is the group >C=N—, their optical isomers and their pharmaceutically acceptable salts. The compounds have anticonvulsive properties.

16 Claims, No Drawings

6-ARYL-S-TRIAZOLO-(4,3-ALPHA)-PYRIDO-(2,3-F)-(1,4)-DIAZEPINES

This is a division, of application Ser. No. 735,894 filed Oct. 26, 1976, now U.S. Pat. No. 4,110,455.

The invention is directed to new 6-aryl-s-triazolo-(4,3-a)-pyrido-(2,3-f)-(1,4)-diazepines of the formula:

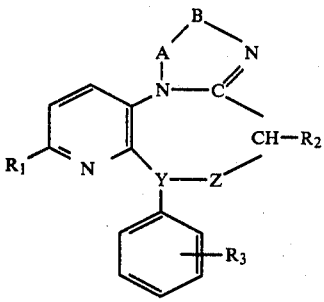

wherein $R_1$ is hydrogen, a halogen atom (preferably of atomic weight 9 to 80), an alkyl group with 1 to 6 carbon atoms, a hydroxy group, an alkoxy group with 1 to 6 carbon atoms, a mercapto group, an alkyl mercapto group having 1 to 6 carbon atoms, an alkylsulfoxido group with 1 to 6 carbon atoms, an alkyl sulfono group with 1 to 6 carbon atoms, an amino group, an aliphatic acylamino group with 2 to 6 carbon atoms, a monoalkylamino group with 1 to 6 carbon atoms, a dialkylamino group with 1 to 6 carbon atoms in each alkyl group or a saturated heterocyclic amino group having 5 to 7 members in the ring including 1 to 2 nitrogen atoms and 0 to 1 oxygen atoms in the ring, $R_2$ is hydrogen, an alkyl group with 1 to 6 carbon atoms, a hydroxy group, an acyloxy group with 2 to 6 carbon atoms, an alkoxy group with 1 to 6 carbon atoms, a mercapto group, an alkylmercapto group with 1 to 6 carbon atoms, a halogen atom (preferably of atomic weight 9 to 80), an amino group, an aliphatic acylamino group with 2 to 6 carbon atoms, a monoalkylamino group with 1 to 6 carbon atoms, a dialkylamino group with 1 to 6 carbon atoms in each alkyl group or a saturated heterocyclic amino group having 5 to 7 members in the ring including 1 to 2 nitrogen atoms and 0 to 1 oxygen atoms in the ring, $R_3$ is hydrogen, an alkyl group with 1 to 6 carbon atoms, an alkoxy group with 1 to 6 carbon atoms or a halogen atom (preferably of atomic weight 9 to 80), the structural part A-B is the group —N=N—, —CH$_2$—NH—, —CO—NR$_4$, —C(SR$_5$)=N—, —C(OR$_5$)=N—, —C(NR$_5$R$_5$)=N—, or —CR$_6$=N—, wherein $R_4$ is hydrogen, an alkenyl group with 2 to 6 carbon atoms, an alkinyl group with 2 to 6 carbon atoms, a hydroxy-alkyl group with 1 to 6 carbon atoms, a ketoalkyl group with 1 to 6 atoms in the alkyl group, a cyanoalkyl group with 1 to 6 carbon atoms an alkyl group with 1 to 6 carbon atoms, or an alkyl group of 1 to 6 carbon atoms substituted by an alkoxy group with 1 to 6 carbon atoms, a dialkylamino group with 1 to 6 carbon atoms in each alkyl group or a saturated heterocyclic amino group having 5 to 7 members in the ring including 1 to 2 nitrogen atoms and 0 to 1 oxygen atoms, $R_5$ is hydrogen or an alkyl group with 1 to 6 carbon atoms, $R_6$ is hydrogen, an alkyl group with 1 to 6 carbon atoms or a haloalkyl group with 1 to 6 carbon atoms, and Y-Z is the group C=N—, >C=N(O), >CH—NH— or >CH—N(OH)— and wherein $R_6$ is other than alkyl if $R_1$ is chlorine, $R_2$ is hydrogen, $R_3$ is hydrogen or halogen and Y-Z is the group >C=N—, their optical isomers and their pharmaceutically acceptable salts.

There can be prepared for example salts with acids such as hydrochloric acid, hydrobromic acid, succinic acid, tartaric acid, fumaric acid, sulfuric acid, citric acid, phosphoric acid, lactic acid, malonic acid, maleic acid, acetic acid, propionic acid, p-toluene sulfonic acid.

As indicated above, the halogen atoms in the compounds of the invention are preferably fluorine, chlorine or bromine, with chlorine and fluorine being particularly preferred. The alkyl, alkenyl, alkinyl and alkylene groups can be branched or straight chain and can contain between 1 to 6 carbon atoms and most preferably, 1 to 4 carbon atoms. Examples of haloalkyl groups ($R_6$) are bromo or chloro $C_1$ to $C_4$ alkyl, especially bromomethyl and chloromethyl. The acyl groups are derived from aliphatic mono- or dicarboxylic with 2 to 6 carbon atoms, e.g., alkanoic acids, alkenoic acids, alkane dioic acids and alkene dioic acids, preferably monocarboxylic acids with 2 to 4 carbon atoms or dicarboxylic acids with 3 to 4 carbon atoms. When there is a substitution in the phenyl nucleus the ortho position is preferred, but the substituents can be present in the meta or para positions. Compounds which have a hydrogen atom attached to a hetero atom can also be present in the tautomeric form.

In addition to the compounds shown in the working examples, illustrative examples of compounds within the invention include 6-(o-chlorophenyl)-4H-s-triazolo-(4,3-a)-pyrido-2(2,3-f)-(1,4)-diazepine, 6-(o-chlorophenyl)-8-fluoro-4H-s-triazolo-(4,3-a)-pyrido-(2,3-f)-(1,4)-diazepine, 6-(o-chlorophenyl)-8-fluoro-4H-s-triazolo-(4,3-a)-pyrido-(2,3-f)-(1,4)-diazepine, 6-(o-fluorophenyl)-8-fluoro-4H-s-triazolo-(4,3-a)-pyrido-(2,3-f)-(1,4)-diazepine, 6-(p-bromophenyl)-8-chloro-4H-s-triazolo-(4,3-a)-pyrido-(2,3-f)-(1,4)-diazepine, 6-(O-chlorophenyl)-8-methyl-4H-s-triazolo-(4,3-a)-pyrido-(2,3-f)-(1,4)-diazepine, 6-phenyl-8-ethyl-4H-s-triazolo-(4,3-a)-pyrido-(2,3-f)-(1,4)-diazepine, 6-phenyl-8-isopropyl-4H-s-triazolo-(4,3-a)-pyrido-(2,3-f)-(1,4)-diazepine, 6-(o-chlorophenyl)-8-butyl-4H-s-triazolo-(4,3-a)-pyrido-(2,3-f)-(1,4)-diazepine, 6-(m-chlorophenyl)-8-sec. butyl-4H-s-triazolo-(4,3-a)-pyrido-(2,3-f)-(1,4)-diazepine, 6-phenyl-8-hexyl-4H-s-triazolo-(4,3-a)-pyrido-(2,3-f)-(1,4)-diazepine, 6-(o-chlorophenyl)-8-hydroxy-4H-s-triazolo-(4,3-a)-pyrido-(2,3-f)-(1,4)-diazepine, 6-phenyl-8-methoxy-4H-s-triazolo-(4,3-a)-pyrido-(2,3-f)-(1,4)-diazepine, 6-(o-chlorophenyl)-8-ethoxy-4H-s-triazolo-(4,3-a)-pyrido-(2,3-f)-(1,4)-diazepene, 6-(o-chlorophenyl)-8-butoxy-4H-s-triazolo-(4,3-a)-pyrido-(2,3-f)-(1,4)-diazepine, 6-(o-chlorophenyl)-8-hexoxy-4H-s-triazolo-(4,3-a)-pyrido-(2,3-f)-(1,4)-diazepine), 6-(o-chlorophenyl)-8-mercapto-4H-s-triazolo-(4,3-a)-pyrido-(2,3-f)-(1,4)-diazepine, 6-phenyl-8-methylthio-4H-s-triazolo-(4,3-a)-pyrido-(2,3-f)-(1,4)-diazepine, 6-(o-chlorophenyl)-8-ethylthio-4H-s-triazolo-(4,3-a)-pyrido-(2,3-f)-(1,4)-diazepine, 6-(o-chlorophenyl)-8-butylthio-4H-s-triazolo-(4,3-a)-pyrido-(2,3-f)-(1,4)-diazepine, 6-(o-chlorophenyl)-8-hexylthio-4H-s-triazolo-(4,3-a)-pyrido-(2,3-f)-(1,4)-diazepine, 6-(o-bromophenyl)-8-methylthio-4H-s-triazolo-(4,3-a)-pyrido-(2,3-f)-(1,4)-diazepine, 6-phenyl-8-propylthio-4H-s-triazolo-(4,3-a)-pyrido-(2,3-f)-(1,4)-diazepine, 6-phenyl-8-sec. butylthio-4H-s-triazolo-(4,3-a)-pyrido-(2,3-f)-(1,4)-diazepine, 6-(o- chlorophenyl)-8-methylsulfoxido-4H-s-triazolo-(4,3-a)-pyrido-(2,3-f)-(1,4)-diazepine, 6-phenyl-8-butylsulfoxido-4H-s-triazolo-(4,3-a)-pyrido-(2,3-f)-(1,4)-diazepine, 6-(o-chlorophenyl)-8-butylsulfoxido-4H-s-triazolo-(4,3-a)-pyrido-(2,3-f)-(1,4)-diazepine, 6-(o-chlorophenyl)-8-hexylsulfoxido-4H-s-triazolo-(4,3-a)-pyrido-(2,3-f)-(1,4)-diazepine, 6-phenyl-8-methylsulfono-4H-s-triazolo-(4,3-a)-pyrido-(2,3-f)-(1,4)-diazepine, 6-(o-chlorophenyl)-8-butylsulfono-4H-s-triazolo-(4,3-a)-pyrido-(2,3-f)-(1,4)-diazepine, 6-(o-chlorophenyl)-8-hexylsulfono-4H-s-triazolo-(4,3-a)-pyrido-(2,3-f)-(1,4)-diazepine, 6-(o-chlorophenyl)-8-amino-4H-s-triazolo-(4,3-a)-pyrido-(2,3-f)-(1,4)-diazepine, 6-(o-chlorophenyl)-8-acetylamino-4H-s-triazolo-(4,3-a)-pyrido-(2,3-f)-(1,4)-diazepine, 6-phenyl-8-propionylamino-4H-s-triazolo-(4,3-a)-pyrido-(2,3-f)-(1,4)-diazepine, 6-(o-chlorophenyl)-8-butyrylamino-4H-s-triazolo-(4,3-a)-pyrido-(2,3-f)-(1,4)-diazepine, 6-phenyl-8-valerylamino-4H-s-triazolo-(4,3-a)-pyrido-(2,3-f)-(1,4)-diazepine, 6-phenyl-8-acetylamino-4H-s-triazolo-(4,3-a)-pyrido-(2,3-f)-(1,4)-diazepine, 6-(o-chlorophenyl)-8-caproylamino-4H-s-triazolo-(4,3-a)-pyrido-(2,3-f)-(1,4)-diazepine, 6-phenyl-8-methylamino-4H-s-triazolo-(4,3-a)-pyrido-(2,3-f)-(1,4)-diazepine, 6-(o-chlorophenyl)-8-methylamino-4H-s-triazolo-(4,3-a)-pyrido-(2,3-f)-(1,4)-diazepine, 6-(o-chlorophenyl)-8-ethylamino-4H-s-triazolo-(4,3-a)-pyrido-(2,3-f)-(1,4)-diazepine, 6-(o-chlorophenyl)-8-butylamino-4H-s-triazolo-(4,3-a)-pyrido-(2,3-f)-(1,4)-diazepine, 6-phenyl-8-hexylamino-4H-s-triazolo-(4,3-a)-pyrido-(2,3-f)-(1,4)-diazepine, 6-phenyl-8-methylethylamino-4H-s-triazolo-(4,3-a)-pyrido-(2,3-f)-(1,4-diazepine, 6-(o-chlorophenyl)-8-diethylamino-4H-s-triazolo-(4,3-a)-pyrido-(2,3-f)-1,4-diazepine, 6-phenyl-8-diisopropylamino-4H-s-triazolo-(4,3-a)-pyrido-(2,3-f)-(1,4)-diazepine, 6-(o-chlorophenyl)-8-dibutylamino-4H-s-triazolo-(4,3-a)-pyrido-(2,3-f)-(1,4)-diazepine, 6-phenyl-8-dihexylamino-4H-s-triazolo-(4,3-a)-pyrido-(2,3-f)-1,4-diazepine, 6-phenyl-8-pyrrolidino-4H-s-triazolo-(4,3-a)-pyrido-(2,3-f)-(1,4)-diazepine, 6-(o-chlorophenyl)-8-morpholino-4H-s-triazolo-(4,3-a)-pyrido-(2m3-f)-(1,4)-diazepine, 6-(o-chlorophenyl)-8-piperidino-4H-s-triazolo-(4,3-a)-pyrido-(2,3-f)-(1,4)-diazepine, 6-phenyl-8-piperazino-4H-s-triazolo-(4,3-a)-pyrido-(2,3-f)-(1,4)-diazepine, 6-(o-chlorophenyl)-8-homopiperazino-4H-s-triazolo-(4,3-a)-pyrido-(2,3-f)-(1,4)-diazepine, 6-phenyl-8-homopiperidino-4H-s-triazolo-(4,3-a)-pyrido-(2,3-f)-1,4-diazepine, 4-methyl-6-(o-chlorophenyl)-8-chloro-4H-s-triazolo-(4,3-a)-pyrido-(2,3-f)-(1,4)-diazepine, 4-ethyl-6-phenyl-8-bromo-4H-s-triazolo-(4,3-a)-pyrido-(2,3-f)-(1,4)-diazepine, 4-butyl-6-(o-chlorophenyl)-8-fluoro-4H-s-triazolo-(4,3-a)-pyrido-(2,3-f)-1,4-diazepine, 4-hexyl-6-phenyl-8-chloro-4H-s-triazolo-(4,3-a)-pyrido-(2,3-f)-(1,4)-diazepine, 4-propionoxy-6-phenyl-8-chloro-4H-s-triazolo-(4,3-a)-pyrido-(2,3-f)-(1,4)-diazepine, 4-butyroxy-6-(o-chlorophenyl)-8-chloro-4H-s-triazolo-(4,3-a)-pyrido-(2,3-f)-(1,4)-diazepine, 4-caproxy-6-phenyl-8-chloro-4H-s-triazolo-(4,3-a)-pyrido-(2,3-f)-(1,4)-diazepine, 4-malonoxy-6-(o-chlorophenyl)-8-chloro-4H-s-triazolo-(4,3-a)-pyrido-(2,3-f)-(1,4)-diazepine, 4-succinoxy-6-phenyl-8-chloro-4H-s-triazolo-(4,3-a)-pyrido-(2,3-f)-(1,4)-diazepine, 4-ethoxy-6-phenyl-8-chloro-4H-s-triazolo-(4,3-a)-pyrido-(2,3-f)-(1,4)-diazepine, 4-butoxy-6-(o-chlorophenyl)-8-chloro-4H-s-triazolo-(4,3-a)-pyrido-(2,3-f)-(1,4)-diazepine, 4-hexoxy-6-(o-chlorophenyl)-8-chloro-4H-s-triazolo-(4,3-a)-pyrido-(2,3-f)-(1,4)-diazepine, 4-mercapto-6-phenyl-8-chloro-4H-s-triazolo-(4,3-a)-pyrido-(2,3-f)-(1,4)-diazepine, 4-methylthio-6-(o-chlorophenyl)-8-chloro-4H-s-triazolo-(4,3-a)-pyrido-(2,3-f)-(1,4)-diazepine, 4-butylthio-6-phenyl-8-chloro-4H-s-triazolo-(4,3-a)-pyrido-(2,3-f)-(1,4)-diazepine, 4-hexylthio-6-(o-chlorophenyl)-8-chloro-4H-s-triazolo-(4,3-a)-pyrido-(2,3-f)-(1,4)-diazepine, 4,8-dichloro-6-(o-chlorophenyl)-8-chloro-4H-s-triazolo-(4,3-a)-pyrido-(2,3-f)-(1,4)-diazepine, 4-amino-6-phenyl-8-chloro-4H-s-triazolo-(4,3-a)-pyrido-(2,3-f)-(1,4)-diazepine, 4-acetylamino-6-(o-chlorophenyl)-8-chloro-4H-s-triazolo-(4,3-a)-pyrido-(2,3-f)-(1,4)-diazepine, 4-butyrylamino-6-phenyl-8-chloro-4H-s-triazolo-(4,3-a)-pyrido-(2,3-f)-(1,4)-diazepine, 4-caproylamino-6-(o-chlorophenyl)-8-chloro-4H-s-triazolo-(4,3-a)-pyrido-(2,3-f)-(1,4)-diazepine, 4-methylamino-6-phenyl-8-chloro-4H-s-triazolo-(4,3-a)-pyrido-2,3-f)-(1,4)-diazepine, 4-butylamino-6-(o-chlorophenyl)-8-chloro-4H-s-triazolo-(4,3-a)-pyrido-(2,3-f)-(1,4)-diazepine, 4-hexylamino-6-phenyl-8-chloro-4H-s-triazolo-(4,3-a)-pyrido-(2,3-f)-(1,4)-diazepine, 4-dimethylamino-6-(o-chlorophenyl)-8-chloro-4H-s-triazolo-(4,3-a)-pyrido-(2,3-f)-(1,4)-diazepine, 4-dibutylamino-6-phenyl-8-chloro-4H-s-triazolo-(4,3-a)-pyrido-(2,3-f)-(1,4)-diazepine, 4-dihexylamino-6-(o-chlorophenyl)-8-chloro-4H-s-triazolo-(4,3-a)-pyrido-(2,3-f)-(1,4)-diazepine, 4-pyrrolidino-6-(o-chlorophenyl)-8-chloro-4H-s-triazolo-(4,3-a)-pyrido-(2,3-f)-(1,4)-diazepine, 4-piperidino-6-phenyl-8-chloro-4H-s-triazolo-(4,3-a)-pyrido-(2,3-f)-(1,4)-diazepine, 4-piperazino-6-(o-chlorophenyl)-8-chloro-4H-s-triazolo-(4,3-a)-pyrido-(2,3-f)-(1,4)-diazepine, 4-morpholino-6-phenyl-8-chloro-4H-s-triazolo-(4,3-a)-pyrido-(2,3-f)-(1,4)-diazepine, 4-homopiperazino-6-phenyl-8-chloro-4H-s-triazolo-(4,3-a)-pyrido-(2,3-f)-(1,4)-diazepine, 6(o-methylphenyl)-8-chloro-4H-s-triazolo-(4,3-a)-pyrido-(2,3-f)-(1,4)-diazepine, 6-(p-ethylphenyl)-8-chloro-4H-s-triazolo-(4,3-a)-pyrido-(2,3-f)-(1,4)-diazepine, 6-(-butylphenyl)-8-chloro-4H-s-triazolo-(4,3-a)-pyrido-(2,3-f)-(1,4)-diazepine, 6-(o-hexylphenyl9-8-chloro-4H-s-triazolo-(4,3-a)-pyrido-(2,3-f)-(1,4)-diazepine, 6(o-methoxyphenyl)-8-chloro-4H-s-triazolo-(4,3-a)-pyrido-2(2,3-f)-(1,4)-diazepine, 6-(o-butoxyphenyl)-8-chloro-4H-s-triazolo-(4,3-a)-pyrido-(2,3-f)-(1,4)-diazepine, 6-(o-hexylphenyl)-8-chloro-4H-s-triazolo-(4,3-a)-pyrido-(2,3-f)-(1,4)-diazepine, 1-amino-6-(o-chlorophenyl)-8-chloro-4H-s-triazolo-(4,3-a)-pyrido-(2,3-f)-(1,4)-diazepine, 1-methylamino-6-phenyl-8-chloro-4H-s-triazolo-(4,3-a)-pyrido-(2,3-f)-(1,4)-diazepine, 1-butylamino-6-(o-chlorophenyl)-8-chloro-4H-s-triazolo-(4,3-a)-pyrido-(2,3-f)-(1,4)-diazepine, 1-hexylamino-6-o-chlorophenyl)-8-chloro-4H-s-triazolo-(4,3-a)-pyrido-(2,3-f)-(1,4)-diazepine, 1-dimethylamino-6(o-chlorophenyl)-8-chloro-4H-s-triazolo-(4,3-a)-pyrido-(2,3-f)-(1,4)-diazepine, 1-dibutylamino-6-phenyl-8-chloro-4H-s-triazolo-(4,3-a)-pyrido-(2,3-f)-(1,4)-diazepine, 1-dihexylamino-6-phenyl-8-chloro-4H-s-triazolo-(4,3-a)-pyrido-(2,3-f)-(1,4)-diazepine, 1-keto-2-vinyl-6-(o-chlorophenyl)-8-chloro-1,2-dihydro-4H-s-triazolo-(4,3-a)-pyrido-(2,3-f)-(1,4)-diazepine, 1-keto-2-methallyl-6-phenyl-8-chloro-1,2-dihydro-4H-s-triazolo-(4,3-a)-pyrido-(2,3-f)-(1,4)-diazepine, 1-keto-2-crotyl-6-phenyl-8-chloro-1,2-dihydro-4H-s-triazolo-(4,3-a)-pyrido-(2,3-f)-(1,4)-diazepine, 1-keto-2-ethinyl-6-phenyl-8-chloro-1,2-dihydro-4H-s-triazolo-(4,3-a)-pyrido-(2,3-f)-(1,4)-diazepine, 1-keto-2-hydroxyemethyl-6-(o-chlorophenyl)-8-chloro-1,2-dihydro-4H-s-triazolo-(4,3-a)-pyrido-(2,3-f)-(1,4)-diazepine, 1-keto-2-hydroxyethyl-6-phenyl-8-chloro-1,2-dihydro-4H-s-triazolo-(4,3-a)-pyrido-(2,3-f)-(1,4)-diazepine, 1-keto-2-hydroxybutyl-6-(o-chlorophenyl)-8-chloro-1,2- dihydro-4H-s-triazolo-(4,3-a)-pyrido-(2,3-f)-(1,4)-diazepine, 1-keto-2-hydroxyhexyl-6-phenyl-8-chloro-1,2-dihydro-4H-s-triazolo-(4,3-a)-pyrido-(2,3-f)-(1,4)-diazepine, 1-keto-2-cyanobutyl-6-phenyl-8-chloro-1,2-dihydro-4H-s-triazolo-(4,3-a)-pyrido-(2,3-f)-(1,4)-diazepine, 1-keto-2-cyanopentyl-6-(o-chlorophenyl)-8-chloro-1,2-dihydro-4H-s-triazolo-(4,3-a)-pyrido-(2,3-f)-(1,4)-diazepine, 1-keto-2-sec. butyl-6-phenyl-8-chloro-1,2-dihydro-4H-s-triazolo-(4,3-a)-pyrido-(2,3-f)-(1,4)-diazepine, 1-keto-2-n-butyl-6-(o-chlorophenyl)-8-chloro-1,2-dihydro-4H-s-triazolo-(4,3-a)-pyrido-(2,3-f)-(1,4)-diazepene, 1-keto-2-hexyl-6-phenyl-8-chloro-1,2-dihydro-4H-s-triazolo-(4,3-a)-pyrido-(2,3-f)-(1,4)-diazepine, 1-keto-2-butoxymethyl-6-phenyl-8-chloro-1,2-dihydro-4H-s-triazolo-(4,3-a)-pyrido-(2,3-f)-(1,4)-diazepine, 1-keto-2-hexoxymethyl-6-(o-chlorophenyl)-8-chloro-1,2-dihydro-4H-s-triazolo-(4,3-a)-pyrido-(2,3-f)-(1,4)-diazepine, 1-keto-2-methoxybutyl-6-phenyl-8-chloro-1,2-dihydro-4H-s-triazolo-(4,3-a)-pyrido-(2,3-f)-(1,4)-diazepine, 1-keto-2-(β-dibutylaminoethyl)-6-phenyl-8-chloro-1,2-dihydro-4H-s-triazolo-(4,3-a)-pyrido-(2,3-f)-(1,4)-diazepine, 1-keto-2-dimethylaminomethyl-6-(o-chlorophenyl)-8-chloro-1,2-dihydro-4H-s-triazolo-(4,3-a)-pyrido-(2,3-f)-(1,4)-diazepine, 1-keto-2-(β-morpholinoethyl)-6-phenyl-8-chloro-1,2-dihydro-4H-s-triazolo-(4,3-a)-pyrido-(2,3-f)-(1,4)-diazepine, 1-keto-2-(β-piperazinoethyl)-6-phenyl-8-chloro-1,2-dihydro-4H-s-triazolo-(4,3-a)-pyrido-(2,3-f)-(1,4)-diazepine, 1-butylthio-6-(o-chlorophenyl)-8-chloro-4H-s-triazolo-(4,3-a)-pyrido-(2,3-f)-(1,4)-diazepine, 1-hexylthio-6-phenyl-8-chloro-4H-s-triazolo-(4,3-a)-pyrido-(2,3-f)-(1,4)-diazepine, 1-methoxy-6-phenyl-8-chloro-4H-s-triazolo-(4,3-a)-pyrido-(2,3-f)-(1,4)-diazepine, 1-butoxy-6-(o-chlorophenyl)-8-chloro-4H-s-triazolo-(4,3-a)-pyrido-(2,3-f)-(1,4)-diazepine, 1-hexoxy-6-(o-chlorophenyl)-8-chloro-4H-s-triazolo-(4,3-a)-pyrido-(2,3-f)-(1,4)-diazepine, 1-bromobutyl-6-phenyl-8-chloro-4H-s-triazolo-(4,3-a)-pyrido-(2,3-f)-(1,4)-diazepine, 1-chloromethyl-6-phenyl-8-chloro-4H-s-triazolo-(4,3-a)-pyrido-(2,3-f)-(1,4)-diazepine, 1-chlorohexyl-6-(o-chlorophenyl)-8-chloro-4H-s-triazolo-(4,3-a)-pyrido-(2,3-f)-(1,4)-diazepine, 1-fluoromethyl-6-phenyl-8-chloro-4H-s-triazolo-(4,3-a)-pyrido-2,3-f)-(1,4)-diazepine, 1-methyl-6-(o-chlorophenyl)-8-chloro-4H-s-triazolo-(4,3-a)-pyrido-(2,3-f)-(1,4)-diazepine, 1-methyl-6-phenyl-8-chloro-4H-s-triazolo-1-ethyl-6-(o-chlorophenyl)-8-chloro-4H-s-triazolo-(4,3-a)-pyrido-(2,3-f)-(1,4)-diazepine, 1-propyl-6-(o-chlorophenyl)-8-chloro-4H-s-triazolo-(4,3-a)-pyrido-(2,3-f)-(1,4)-diazepine, 1-isopropyl-6-phenyl-8-chloro-4H-s-triazolo-(4,3-a)-pyrido-(2,3-f)-(1,4)-diazepine, 1-butyl-6-phenyl-8-chloro-4H-s-triazolo-(4,3-a)-pyrido-(2,3-f)-(1,4)-diazepine, 1-sec. butyl-6-(o-chlorophenyl)-8-chloro-4H-s-triazolo-(4,3-a)-pyrido-(2,3-f)-(1,4)-diazepine, 1-hexyl-6-(o-chlorophenyl)-8-chloro-4H-s-triazolo-(4,3-a)-pyrido-(2,3-f)-(1,4)-diazepine.

The compounds of the invention are pharmacodynamically active. More particularly, they have anxiolytic spasmolytic and sedative properties. In part, they are also antiphlogistic and are protectives against ulcers. In anxiolytic activity (measured by anticonvulsive activity at Cardiazol-shock in the mouse) this is not disturbed by undesired side effects as particularly ataxia (tested on the rotating rod) or sedation (Evipan sleep test).

The compounds of the invention can be prepared by methods which are known in themselves, such as:

(a) reacting a compound of the formula

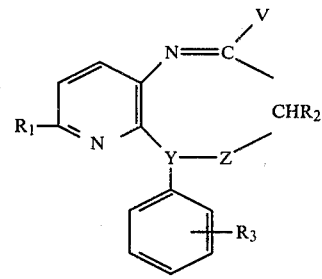

wherein $R_1$, $R_2$, $R_3$ and $R_4$ are as defined above and V is a hydroxy, mercapto, amino, benzylamino, $C_1$ to $C_5$ alkoxy, $C_1$ to $C_5$ alkylthio, $C_1$ to $C_5$ alkylamino or di $C_1$ to $C_5$ alkylamino group or is the radical $-NH-NHR_4$ wherein $R_4$ is as defined above with a compound of the general formula

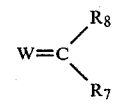

wherein in formula III W is oxygen, sulfur, >NH or $(R_5O)_2$ or $(R_5S)_2$ and the radicals $R_7$ and $R_8$ are the same or different and can be hydrogen, the radical $-NR_4-NH_2$, a hydroxy group, a mercapto group, a halogen atom, an amino group, a lower alkylamino group, a di-lower alkyl amino group, an imidazolyl group, a lower alkoxy group or a lower alkylmercapto group or $R_7$ and $R_8$ can be joined together to indicate a sulfur atom. One of the radicals $R_7$ and $R_8$ also can be an alkyl group with 1 to 6 carbon atoms, a haloalkyl group with 1 to 6 carbon atoms or together with W=C can also form the cyano group or the NO group and in a given case in the compounds obtained, the radicals $R_1$ and/or $R_2$ or the groups $-A-B$ or $Y-Z$ can be converted to another group of the invention within such definition, or (b) starting with a compound of formula I and exchanging in this compound one or more of the substitutents $R_1$, $R_2$, $R_4$ and $R_5$ for another substitutent within the meanings set forth above, or (c) a comound of formula I where Y=Z is the group >C=N— or >C=NO— is reduced to compounds in which Y-Z is the group >C=N—, >CH—NH— or >CH—N(OH), or (d) a compound of formula I where $R_2$ is hydrogen and Y-Z is the group >C=N(O) and the remaining symbols have their given meaning is rearranged into compounds wherein $R_2$ is a hydroxy group or an acyloxy group with 2 to 6 carbon atoms and Y-Z is the group >C=N—, and in a given case the acyl group present can be saponified to form the hydroxyl group, or (e) a compound of formula I wherein Y-Z is the group >C=N and the remaining symbols have the meanings set forth above is converted to the corresponding N-oxide.

Process (a) can be carried out in the melt or in the presence of a solvent or suspension agent at temperatures between 0° and 250° C., preferably between 20° and 160° C. or also between 20° and 100° C. As solvents or suspension agents there can be used for example, water, aliphatic alcohols (e.g., methyl alcohol, ethyl alcohol, isopropyl alcohol, propyl alcohol, butyl alcohol, hexyl alcohol), dioxane, tetrahydrofuran, cycloalkanols, e.g., cyclohexanol, etheric solvents such as diethylene glycol dimethyl ether or diethylene glycol diethyl ether, amides such as N,N,N',N',N'',N''-hexamethyl phosphoric acid triamide, dimethyl sulfoxide, dimethyl formamide, glacial acetic acid, chloroform, hydrocarbons such as toluene, xylene and benzene, chlorohydrocarbons such as chlorobenzene, nitrobenzene or also an excess of reagent II. In a given case there can be added condensation agents such as polyphosphoric acids, esters of polyphosphoric acids, esters of polyphosphoric acids, sulfuric acid, acetic acid, zinc chloride, pyridine, salts of pyridine or tertiary amines. In case both $R_6$ and $R_7$ are hydrogen process (a) can be carried out in a given case also in the presence of iron (III) chloride solution or lead (IV) acetate, for example in ethanolic iron (III) chloride solution under reflux or with lead (IV) acetate heated in benzene or glacial acetic acid.

Reactant III can also be used in excess.

The reaction of a compound of formula III with a compound of formula II progresses in a given case by way of an open intermediate stage which can also be isolated in a given case.

In case in process (a) there is added as a compound of formula II compounds of the following formula:

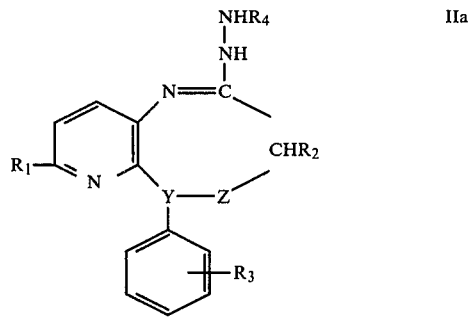

(where $R_1$, $R_2$, $R_3$, $R_4$ and Y-Z are as defined above) then there are particularly used as reaction

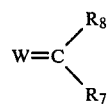

III compounds of formula III where Y is oxygen, sulfur, >NH, $(R_5O)_2$ or $(R_5S)_2$ and the groups $R_7$ and $R_8$ are the same or different and are hydrogen, a hydroxy group, a mercapto group, a halogen atom, an amino group, a lower alkyl group, a dilower alkyl group, an imidazolyl group, a lower alkoxy group or a lower alkylmercapto group or together are a sulfur atom, wherein one of the radicals $R_7$ or $R_8$ also can be an alkyl group with 1 to 6 carbon atoms or together with W=C can also form the cyano group or the NO group. In case one of the radicals $R_7$ or $R_8$ forms the NO group with W=C, is a matter of nitrosyl compounds, particularly nitrous halides (e.g., nitrous chloride or bromide), esters of nitrous acid (particularly lower alkyl esters, e.g., ethyl nitrite) as well as nitrous acid or anhydride.

Examples are orthoformic acid tri $C_1$ to $C_6$ (particularly $C_1$ to $C_4$ alkyl esters), e.g., trimethyl orthoformate, triethyl orthoformate, tributyl orthoformate and trihexyl orthoformate, ortho carbonic acid tetra $C_1$ to $C_6$ (particularly $C_1$ to $C_4$) alkyl esters, e.g., tetramethyl orthocarbonate, tetraethyl orthocarbonate, tetrabutyl ortho carbonate, tetrahexyl orthocarbonate, $C_1$ to $C_5$ (particularly $C_1$ to $C_3$) - alkylacetic acid - ortho $C_1$ to $C_4$ alkyl esters, $C_1$ to $C_5$ (particularly $C_1$ to $C_3$) haloalkylacetic acid ortho $C_1$ to $C_4$ alkyl esters (wherein the halogen is Cl or bromine and preferably is in the alpha position), $CS_2$, N,N-carbonyldiimidazole, nitrous acid or its alkali salts, e.g., sodium nitrite and potassium nitrite, and its anhydride.

In case compounds of formula II are used wherein V is a hydroxy or mercapto group then the compound of formula II, particularly where V=O, is present chiefly in the tautomeric form which has the formula:

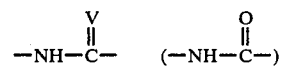

Corresponding tautomeric forms or tautomeric equilibriums can also be present for the remaining meanings of V (V=monoalkylamino, $NH_2$, benzylamino). This is without significance for the reaction according to the process.

As lower alkylthio or alkoxy groups V is preferably the methylthio or ethylthio group or the methoxy or ethoxy group. These groups can be activated by a substitutent. Such activated groups include, for example, the o- or p-nitrobenzyloxy groups. As monosubstituted amino groups V is especially a lower alkylamino group, such as the methylamino group or an aralkylamino group such as the benzylamino group. As disubstituted amino groups V is especially a lower dialkylamino group such as the dimethylamino group.

In case V does not represent the radical —NH—NHR but has the remaining meanings, there can be used as compounds of formula III hydrazine derivatives of the formula $H_2N$—$NR_4$—COR wherein R is preferably hydrogen, a $C_1$ to $C_6$ alkyl group, a $C_1$ to $C_6$ alkoxy group, a $C_1$ to $C_6$ alkylmercapto group, the group —$NR_5R_5$ or a hydroxy or mercapto group.

In regard to process (b):

In case $R_1$ and/or $R_2$ is a halogen atom, preferably chlorine or bromine, then such a halogen atom can be exchanged for a hydroxy or mercapto or alkoxy or alkylmercapto or amino or substituted amino group as defined for formula I. Hereby a compound of formula I wherein $R_1$ and/or $R_2$ is a halogen atom is reacted with ammonia or an ammonia-yielding compound (hexamethylenetetramine, ammonium carbonate, alkali amide, e.g., sodamide, or ammonium salts of weak acids, e.g., ammonium acetate) or an alkylamine with alkyl groups of 1 to 6 carbon atoms or a dialkylamine with alkyl groups of 1 to 6 carbon atoms or wherein the alkyl radicals of this dialkylamino group together with the nitrogen atom and, in a given case, a further nitrogen atom or oxygen atom also can form a saturated 5 to 7 membered ring. This reaction can be carried out for example in an inert solvent or suspension agent such as tetrahydrofuran, dioxane, ethanol, n-propanol, isopropanol, methanol, n-butanol, dimethyl sulfoxide or dimethyl formamide as well as in the presence of an excess of the basic reactant at temperatures between 0° and 200° C., preferably 40° to 130° C. There can be added acid acceptors such as potassium carbonate, sodium bicarbonate, sodium carbonate, calcium carbonate, non-quaternized tertiary amines such as diisopropylmethyl amine for example or also basic ion exchangers.

To convert an acylamine the process also can be operated for example in the presence of sodium hydride, sodamide, butyl lithium, etc., as solvents in this case there are used only those which contain no functional groups such as dioxane, dimethyl formamide or benzene. Hereby the temperatures in general lie somewhat below those given above, for example, between 20° and 100° C.

The exchange of halogen against the hydroxyl group takes place for example in alcoholic or aqueous-alcoholic medium between 20° and 150° C. with addition of a metal hydroxide such as NaOH, KOH, AgOH (or $Ag_2O$) or other alkaline reacting salts such as potassium carbonate or sodium carbonate. In the case of the exchange for a mercapto group the reaction is with sulfides, especially alkali sulfides, e.g., sodium sulfide or potassium sulfide or alkaline earth sulfides, e.g., calcium sulfide.

In the case of the exchange for alkoxy or alkylmercapto groups the reaction is carried out with the corresponding alcohols or alkyl mercaptans in, for example, polar solvents such as alcohols, e.g., methyl alcohol, ethyl alcohol or isopropyl alcohol or acetone with addition of acid binding agents such as alkali, e.g, sodium hydroxide or potassium hydroxide, tertiary amines or silver oxide. The alcohol is preferably used in excess. Preferably the temperature is between 20° and 150° C. In the case of the exchange of $R_2$=halogen against the above-named groups, the temperature is preferably between 0° and 50° C. Basically for the exchange reactions given here there can also be used all of the acid binding agents given in the reaction with amines.

In case $R_1$ and/or $R_2$ is an amino group then such a group can be exchanged for a hydroxy group or a halogen atom. This reaction takes place for example in aqueous, alcoholic or aqueous-alcoholic medium at temperatures between 0° and 100° C. in the presence of acids, e.g., hydrochloric acid or sulfuric acid, and addition of alkali nitrites, e.g., sodium nitrite or potassium nitrite, alkyl nitrites, e.g., ethyl nitrite or butyl nitrite, or $N_2O_3$ (or nitrous gases). In the case of the exchange against Hal there is used an excess of the acid concerned, e.g., hydrochloric acid or concentrated hydrofluoric acid or the action of a halogenation agent takes place, for example in combination with a diazotization (Sandmeyer reaction or modified Sandmeyer process) in the presence of the corresponding halogen ions and/or the corresponding copper (I) salt or also fluoroborate ions.

In case $R_1$ and/or $R_2$ is a hydroxy group or an alkoxy group then such a group can be exchanged against a halogen atom. This reaction can be carried out in inert solvents such as dioxane, chloroform, hydrocarbons, such as benzene and toluene or other solvents such as nitrobenzene, diethyl ether, acetone, dimethyl formamide, or ethylene dichloride with halogenation agents such as phosphorus pentachloride, phosphorus oxychloride, thionyl chloride, titanium tetrachloride, triphenylphosphine dichloride as well as halogen phosphoric acid esters such as diethoxy phosphorus trichloride at temperatures between 20° and 150° C.

In case $R_1$ is an alkylmercapto group, this can be oxidized to an alkylsulfoxide group with 1 to 6 carbon atoms or an alkylsulfono group with 1 to 6 carbon atoms. This reaction can be carried out for example in inert solvents such as alcohols, e.g., ethyl alcohol, acetone, acetic acid or acetic anhydride, as well as the corresponding mixtures with water as well as in chlorinated hydrocarbons, by oxidation with hydrogen peroxide, alkyl peroxides (e.g., tert. butyl peroxide) or peroxy acids (e.g., peracetic acid or m-chloro-perbenzoic acid) at temperatures between 0° and 150° C.

In compounds of formula I wherein $R_1$ is a hydroxy, mercapto or amino group, these groups can be alkylated. Likewise the groups $R_4$ and $R_5$ can be introduced by alkylation into compounds of formula I wherein $R_4$ and/or $R_5$ is hydrogen, while the remaining symbols have the designated meanings. Likewise compounds of formula I wherein $R_2$ is hydrogen, $NH_2$, a hydroxy or a mercapto group can be alkylated to compounds wherein $R_2$ now is an alkyl group or an alkoxy or alkylmercapto group. These alkylations take place in a manner known in itself. As alkylation agents there can be used for example esters of the formula $R_4Hal$, $Ar$-$SO_2OR_4$ and $SO_2(OR_4)_2$ wherein Hal is a halogen atom (especially chlorine, bromine or iodine and Ar is an aromatic group as for example a napthyl or phenyl group which in a given case is substituted by one or more lower alkyl groups and $R_4$ is an alkyl group with 1 to 6 carbon atoms or, with the exception of hydrogen, can have the other stated meanings for $R_4$. Examples are p-toluenesulfonic acid $C_1$ to $C_6$ alkyl esters, e.g., methyl p-toluenesulfonate, ethyl p-toluenesulfonate or hexyl p-toluenesulfonate, lower $C_1$ to $C_6$ dialkyl sulfates, e.g., dimethyl sulfate, diethyl sulfate or dihexyl sulfate, and the like. The alkylation reaction is undertaken in a given case with addition of customary acid binding agents, such as alkali carbonates, e.g., sodium carbonate, pyridine or other customary tertiary amines at temperatures between 0° and 150° C. in inert solvents such as alcohols, e.g., ethyl alcohol, dioxane, dimethyl formamide, dimethyl sulfoxide, aromatic hydrocarbons such as benzene or toluene or acetone.

In a given case the alkylation can also proceed in such manner that first an alkali compound is produced from the alkylating compound while reacting in an inert solvent such as dioxane, dimethyl formamide, benzene or toluene with an alkali metal, alkali hydride or alkali amide (especially sodium or sodium compounds, e.g., sodium hydride or sodamide) at temperatures between 0° and 150° C. and then adding the alkylating agent (for example in case one starts with a compound where $R_2$ is hydrogen).

In compounds of formula I wherein $R_2$ is a hydroxy group this hydroxy group can be acylated with an acyl group having 2 to 6 carbon atoms. Likewise with compounds of formula I in case $R_1$ and/or $R_2$ is an amino group this $NH_2$ group can be acylated by an acid group with 2 to 6 carbon atoms.

The acylation can take place in inert solvents or suspension agents such as dioxane, dimethyl formamide, benzene or toluene at temperatures between 0° and 200° C., preferably 20° to 150° C.

As acylating agents there can be used ketenes, e.g., ketene per se as well as acid halides, acid anhydrides or acid esters of aliphatic carboxylic acids with 2 to 6 carbon atoms, e.g., acetyl chloride, propionyl chloride, butyryl chloride, caproyl chloride, acetic anhydride, monomethyl malonate or monoethyl succinate, in a given case with addition of an acid binding agent such as alkali carbonates, alkali hydroxides, alkali alcoholates or a tertiary amine, for example triethylamine. As the esters there are employed especially those with lower aliphatic alcohol, e.g., methyl alcohol, ethyl alcohol or butyl alcohol. In the acylation there can also be provided that there is first produced from the reacting compound of formula I wherein $R_2$=OH or $NH_2$ and- /or $R_1$=$NH_2$ an alkali compound while the reaction is carried out in an inert solvent such as dioxane, dimethyl formamide, benzene or toluene with an alkali metal, alkali hydride or alkali amide (especially sodium or sodium compounds) at temperatures between 0° and 150° C. and then adding the acylating agent.

In a given case the acylating agent can also be used in excess. It is also possible in many cases to acylate directly with an aliphatic carboxylic acid having 2 to 6 carbon atoms with addition of corresponding condensation agent such as, e.g., dicyclohexylcarbodiimide or for example 1-ethyl-2-ethoxycarbonyl dihydroquinoline.

In place of the alkylation and acylation agents mentioned there can also be used other chemically equivalent agents (see for example L. F. and Mary Fieser, "Reagents for Organic Synthesis," Vol. 1, pages 1303-4 and Vol. 2, page 471). It should be understood that acyl groups present in the compounds of formula I also can be split off again in known manner.

Acyl groups present can be split off again in known manner. This splitting takes place for example in aqueous, aqueous-alcoholic medium or also in mixtures of acetone with water and/or alcohols or also in pure alcohols in the presence of alkali such as potassium hydroxide, sodium ethylate, potassium carbonate or tertiary amines or also secondary or primary amines wherein these materials are preferably present in equivalent amounts. The splitting can also take place in low molecular weight alcohols, e.g., ethyl alcohol, with addition of small amounts of strong acids (hydrochloric acid, sulfuric acid, toluenesulfonic acid). The temperature for the splitting of the acyl groups generally is between 0° and 150° C.

Particularly process (b) consists of reacting a compound of formula I wherein $R_1$ is chlorine or bromine and the remaining symbols have their stated meanings with a compound of the formula H-T or its alkali salt wherein T is a hydroxy or mercapto group, a $C_1$ to $C_6$ alkylmercapto group, a $C_1$ to $C_6$ alkoxy group, an amino group, a $C_2$ to $C_6$ acylamino group, a $C_1$ to $C_6$ monoalkylamino group or a dialkylamino group with $C_1$ to $C_6$ groups wherein the alkyl groups of this dialkylamino group together with the N-atom and in a given case a further nitrogen atom or an oxygen atom can form a saturated 5 to 7 membered ring or that a compound of formula I which has at least one free hydroxy, mercapto, amino or imino group (group —CO—NH—) is acylated or reacted with a compound of formula $R_4'$-S wherein $R_4'$ has the same meaning as that of $R_4$ except for hydrogen and S is chlorine, bromine or iodine, the group $(SO_2)_{\frac{1}{2}}O$— or the group $ArSO_2O$— and Ar is an aromatic group as for example phenyl or naphthyl, in a given case substituted by a lower alkyl group.

In regard to process (c):

The reduction according to process (c) is carried out for example in inert solvents such as dioxane, dimethyl formamide, ether, tetrahydrofuran, chloroform, aromatic hydrocarbons or alcohols by means of catalytic hydrogenation (noble metal or nickel catalysts, for example Raney nickel, platinum or palladium), by means of metal hydrides, e.g., sodium hydride, complex alkali hydrides (for example sodium borohydride, lithium aluminum hydride or alkoxy derivatives of lithium aluminum hydride), by means of nascent hydrogen (iron-glacial acetic acid, zinc-hydrochloride acid, aluminum-KOH or aluminum-mercury-water), by means of reducing compounds of elements of group IV or V of the periodic system (for example titanium trichloride, phosphorus trichloride, esters of phosphorus acid, especially the lower alkyl esters, e.g., trimethyl phosphite) or by means of dimethyl sulfoxide. The last named reducing agent is particularly suited for reduction of N-oxides (Y-Z=>C=N→O) into the corresponding compounds of formula I wherein Y-Z is the group >C=N—. As solvents there can be used particularly dioxane, benezene or toluene, as temperatures preferably 50° to 150° C. Also it is possible to reduce the N-oxides for example by catalytic hydrogenation.

The temperatures for process (c) generally lie between 0° and 200° C., preferably 20°-100° C. In a given case the process can also be operated under pressure (for example up to 50 atmospheres absolute).

If there is used as the starting material a compound wherein Y-Z is the group >C=N(O)— there can be obtained by the reduction with lithium aluminum hydride or with alkoxy derivatives of lithium aluminum hydride compounds of formula I wherein Y-Z is the group >C—N(OH).

In regard to process (d):

This process leads to compounds of formula I wherein $R_2$ is a hydroxy group or an acyloxy group with 2 to 6 carbon atoms while the remaining symbols have their stated meanings. There are employed compounds of formula I wherein $R_2$ is hydrogen and the group Y-Z is the group >C=N(O)— and this treated in a low molecular weight aliphatic acid anhydride (for example acetic anhydride) in a given case in admixture with other inert solvents. Thereby a rearrangement occurs according to which the oxygenation attached to the nitrogen forms a hydroxyl group on the adjacent carbon atom. Subsequently in the presence of the acid anhydride this hydroxyl group in most cases is acylated. The rearrangement takes place at temperatures between 0° and 150° C., especially 0° to 100° C. The acyl group can be split off in customary manner, for example in aqueous, aqueous-alcoholic medium or also in mixtures of acetone with water and/or alcohols or also in pure alcohols, e.g., ethyl alcohol, in the presence of alkali (e.g., potassium hydroxide, sodium ethylate or potassium carbonate) or also in the presence of tertiary amines or secondary or primary amines. Likewise splitting is possible in lower alcohols, e.g., ethyl alcohol, with addition of small amounts of strong acids (such as HCl, sulfuric acid or toluenesulfonic acid). The temperatures for the splitting for example is between 0° and 150° C.

Process (e):

The oxidation of compounds of formula I wherein Y-Z is the group >C=N—, the remaining symbols having the stated meanings, to the corresponding N-oxides can be carried out for example in inert solvents such as chloroform or other chlorohydrocarbons, benzene, toluene, acetone or ethyl acetate with hydrogen peroxide, a conventional aliphatic or aromatic per acid (peracetic acid, perbenzoic acid, m-chloroperbenzoic acid) or other monosubstitution products of hydrogen peroxide such as alkyl peroxides (for example tert. butyl peroxide) at temperatures between 0° and 150° C., preferably 0° to 100° C.

Basic compounds of formula I can be converted into their salts by conventional methods. As anions for these salts there can be employed the known and therapeutically usable (pharmaceutically acceptable) acid residues. For example, there can be used acids such as sulfuric acid, phosphoric acid, hydrohalic acids, e.g., hydrochloric acid or hydrobromic acid, ethylenediamine tetraacetic acid, sulfamic acid, benzene sulfonic acid, p-toluene sulfonic acid, camphor sulfonic acid, methane sulfonic acid, quaiazulene sulfonic acid, maleic acid, fumaric acid, oxalic acid, tartaric acid, lactic acid, citric acid, ascorbic acid, glycolic acid, salicyclic acid, acetic acid, propionic acid, gluconic acid, benzoic acid, acetamidoacetic acid, hydroxyethane sulfonic acid, malonic acid.

If the compounds of formula I contain acid groups they can be converted in customary manner to their alkali, e.g., sodium or potassium, ammonium or substituted ammonium salts. As substituted ammonium salts there are especially recommended salts of tertiary alkylamines, lower aminoalcohols such as bis and tris (hydroxyalkyl) amines (having alkyl residues with 1 to 6 carbon atoms) such as triethyl amine, ethanolamine, diethanolamine, dipropanolamine, triethanolamine, tributyl amine.

The free bases can be produced again from the salts of the compounds in customary manner, for example, by treatment of a solution in an organic medium, such as alcohols (e.g., methanol, ethanol or isopropanol) with soda or soda lye (caustic soda solution).

Compounds of formula I can also be present in tautomeric forms. The compounds in this case can be present completely or partially in one of the possible tautomeric forms. Generally, under the normal working and storing conditions there is present an equilibrium.

Those compounds of formula I which contain asymmetric carbon atoms and as a rule result as racemates, can be split into the optically active isomers in known manner with the help of an optically active acid. However, it is also possible to employ from the beginning an optically active starting material whereby a correspondingly optically active or diastereomer form is obtained as the end product.

The compounds of the invention are suitable for the production of pharmaceutical compositions. The pharmaceutical compositions or medicaments can contain one or more of the compounds of the invention or mixtures of the same with other pharmaceutically active materials. For the production of pharmaceutical preparations there can be used the customary pharmaceutical carriers and assistants. The medicines can be employed enterally, parenterally, orally or perlingually. For example, dispensing can take place in the form of tablets, capsules, pills, dragees, plugs, salves, jellies, cremes, powders, liquids, dusts or aerosols. As liquids there can be used, for example, oily or aqueous solutions or suspensions, emulsions, injectable aqueous and oily solutions or suspensions.

For example there can be used compounds of formula I in which the symbols $R_1$ to $R_5$ as well as Y-Z and A-B have the following meanings.

$R_1$: $NH_2$ lower dialkylamino groups (alkyl groups of 1 to 3 carbon atoms, e.g., methyl, ethyl, propyl, isopropyl), morpholino group, piperidino group, hydroxyethylamino group, pyrrolidino group, chlorine, bromine, fluorine, methylmercapto or dimethylamino. Preferably, $R_1$ is chlorine.

$R_2$: Hydrogen, an alkyl group with 1 to 3 carbon atoms, e.g., methyl, ethyl, propyl or isopropyl, a hydroxy group or an acyloxy group wherein the acyl group is derived from an aliphatic saturated, acyclic mono or dibasic acid with 2 to 4 carbon atoms, e.g., it is derived from acetic acid, propionic acid, butyric acid, oxalic acid, malonic acid or succinic acid. Preferably $R_2$ is hydrogen.

$R_3$: Hydrogen, fluorine, chlorine or bromine, wherein the ortho position is preferred. Preferably $R_3$ is hydrogen, chlorine or fluorine.

$R_4$: Hydrogen, an alkyl group with 1 to 4 carbon atoms, e.g., methyl, ethyl, propyl, isopropyl, butyl, sec. butyl (with methyl and isopropyl being preferred), an alkenyl group with 2 to 4 carbon atoms, e.g., vinyl, allyl, methallyl, crotyl or butenyl-2 (with allyl and butenyl-2 being preferred) or a hydroxyalkyl group with 2 to 4 carbon atoms, e.g., hydroxyethyl, hydroxypropyl or hydroxybutyl (the preferred hydroxyalkyl group is hydroxyethyl) or a dialkylaminoethyl, dialkylaminopropyl or dialkylaminoisopropyl group wherein the alkyl radical preferably contains 1 to 4 carbon atoms (e.g., dimethylaminoethyl, diethylaminoethyl, dipropylaminoethyl, diisopropylaminoethyl, dibutylaminoethyl, dimethylaminopropyl, diethylaminopropyl, dimethylaminoisopropy, dibutylaminoisopropyl) or for example, compounds where the two alkyl groups together with the nitrogen atom and a further nitrogen atom or an oxygen atom can form a heterocyclic ring, e.g., a piperidino, piperazino, pyrrolidino, homopiperazino or morpholino ring (for example morpholinoethyl, piperidinoethyl, morpholinopropyl, piperidinopropyl, pyrrolidinoethyl). Preferably $R_4$ is hydrogen.

$R_5$: Hydrogen or an alkyl group with 1 to 4 carbon atoms, e.g., methyl, ethyl, propyl, isopropyl, butyl, isobutyl or sec. butyl. Preferably $R_5$ is hydrogen or methyl.

$R_6$: Hydrogen or an alkyl group with 1 to 4 carbon atoms, e.g., methyl, ethyl, propyl, isopropyl, butyl, sec. butyl. Preferably $R_6$ is hydrogen.

A-B: $-CH=N-$, $-CO-NH-$, $-CO-NR_4$ wherein $R_4$ is as defined previously, $-C(SCH_3)=H-$ or $-C(OH)=N-$. Preferably A-B is $CH=N-$.

Especially favorable activity is possessed by compounds in which $R_1$ is chlorine, bromine, fluorine or a $C_1$ to $C_4$ alkylmercapto group, e.g., methylmercapto, ethylmercapto, propylmercapto, butylmercapto (the most preferred alkylmercapto group is methylmercapto), $R_2$ is hydrogen, $R_3$ is hydrogen or chlorine, A-B is the group $-CR_6=N-$ (wherein $R_2$ is especially H, methyl, ethyl, propyl, isopropyl, butyl, isobutyl or tertiary butyl) and Y-Z is the group $>C=N-$.

Starting materials of formula II wherein $R_1$ is halogen or amino, or in a given case substituted amino and $R_4$ is hydrogen, an alkyl, alkenyl, hydroxyalkyl or dialkylaminoalkyl group are known for example from German Offenlegungsschrift No. 2,259,471 (and related von Bebenburg U.S. patent application Ser. No. 507,605 filed Sept. 19, 1974) and German Offenlegungsschrift No. 2,419,386 (and related von Bebenburg U.S. Pat. No. 3,941,775). The entire disclosures of von Bebenburg U.S. application Ser. No. 507,605 and von Bebenburg U.S. Pat. No. 3,941,775 are hereby incorporated by reference and relied upon.

Independent therefrom collectively the starting materials of formula II can be obtained as follows:

The basic compounds for the production of these compounds are the compounds described in German Offenlegungsschrift No. 2,259,471 (page 21 et seq.), von Bebenburg application No. 507,605 (page 25 et seq.), German Offenlegungsschrift No. 2,419,386 (page 24 et seq.) and von Bebenburg Pat. No. 3,941,775 (col. 15 et seq.) having the following formula:

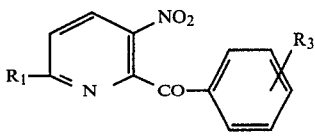

wherein $R_1$ is a halogen atom or an amino or in a grain case substituted amino group and $R_3$ can have the previously stated meanings.

From those compounds of formula IV wherein $R_1$ is a halogen atom, especially chlorine or bromine, by reaction with lower alkali alcoholates, e.g., sodium ethylate, alkali hydroxides, e.g., sodium hydroxide, or alkali hydrosulfides, e.g., sodium hydrosulfide, there can be obtained compounds of the formula IV wherein $R_1$ is a $C_1$ to $C_6$ alkoxy group, a hydroxy group or a mercapto group. These reactors as a rule are carried out in alcohols (e.g., methanol, ethanol), in a given case with an excess of the basic component at temperatures between 0° and 250° C.

Those compounds where $R_1$ is an alkylmercapto group and then obtained from compounds of formula IV wherein

is a mercapto group by conventional alkylation. From compounds of formula IV where $R_1$ is an alkylmercapto group there can then be obtained the corresponding sulfoxides, for example, by oxidation with hydrogen peroxide or dilute nitric acid or with stronger oxidation agents as, for example, with potassium permanganate there can be obtained the corresponding sulfones.

By reaction of compounds of formula IV wherein $R_1$ is a halogen atom, especially chlorine or bromine, with compounds which have active $CH_2$— or $CH$— groups, for example malonic acid esters, e.g., diethyl malonate, or esters of alkyl substituted malonic acid there are obtained compounds of formula IV wherein $R_1$ is a $C_1$ to $C_6$ alkyl group. For example, there is reacted for this purpose the halopyridine of formula IV in dioxane with the alkali derivative of the corresponding alkylated malonic acid diester (diethyl ester). The crude condensation product, which is present in the form of its sodium salt is then, without further purification, saponified and at the same time decarboxylated (two carboxy groups are split off). This saponification and decarboxylation is accomplished for example by boiling for several hours with aqueous ethanolic hydrochloric acid. Subsequently, the product is evaporated to dryness. The thus obtained preliminary product in most cases is sufficiently pure for the further reactions. In a given case it can also be recrystallized from a customary solvent.

Unless otherwise indicated all parts and percentages are by weight.

These reactions are illustrated by the following examples:

2-BENZOYL-3-NITRO-6-METHOXYPYRIDINE 60 grams of 2-benzoyl-3-nitro-6-chloropyridine were added in portions to a solution of 10 grams of sodium metal in 500 ml. of methanol at 50° C. with stirring, whereby the temperature gradually increased. Then the mixture was heated under reflux for four hours and subsequently treated with two liters of water. The precipitated crystals were filtered off with suction after one hour and recrystallized from methanol.

Yield: 51 grams; M.P. 126°–128° C.

2-BENZOYL-3-NITRO-6-MERCAPTOPYRIDINE

There were added to a mixture of 200 grams of 2-benzoyl-3-nitro-6-chloropyridine and 1 liter of ethanol with stirring 120 grams of sodium hydrogen sulfide monohydrate in portions. The temperature increased to 55° C. After the addition boiling was carried out for one hour at reflux, the solution filtered and acidified with glacial acetic acid. Upon addition of water, the reaction product crystallized. It was dissolved in dilute sodium hydroxide solution, the solution filtered, and the mercapto compound again precipitated with glacial acetic acid.

Yield: 140 grams; M.P. 110° to 115° C. (Decomposition)

2-BENZOYL-3-NITRO-6-METHYLMERCAPTO-PYRIDINE 150 grams of 2-benzoyl-3-nitro-6-mercaptopyridine were dissolved in a solution of 45 grams of sodium hydroxide in 2.5 liters of water and hereto there was added dropwise at 35° C. with stirring 90 ml. of dimethyl sulfate. Then the composition was stirred for one hour at 40° C. After cooling the precipitated crystals were filtered off with suction and recrystallized from 1.8 liters of methanol.

Yield: 144 grams; M.P. 110° to 112° C.

2-BENZOYL-3-NITRO-6-METHYLPYRIDINE

They were added to a solution of 16.8 grams of diethyl malonate in 75 ml. of dioxane with stirring and under a nitrogen atmosphere 3.3 grams of sodium hydride (80%) and then stirring continued for 15 minutes more. Then there were added in portions 26.3 grams of 2-benzoyl-3-nitro-6-chloropyridine and then stirring was continued at 70° C. for two hours more. The precipitated deeply colored sodium salt of the dicarbethoxymethyl compound was filtered off with suction. Five grams of this compound were boiled under reflux in a mixture of 25 ml. of concentrated hydrochloric acid and 25 ml. of methanol for 90 minutes, the solution filtered hot and the filtrate treated with water to the point of turbidity. The desired product crystallized out.

Yield: 2 grams; M.P. 101° to 103° C.

Those compounds of formula IV wherein $R_1$ is a hydroxy group can also be obtained from the corresponding 2-(α-cyanobenzyl)-3-nitro-6-chloropyridine derivative (see German Offenlegungsschrift No. 2,259,471, page 21 and related von Bebenburg U.S. application Ser. No. 507,605, pages 24–25) by treatment with alkaline hydrogen peroxide as shown by the following example:

2-BENZOYL-3-NITRO-6-HYDROXYPYRIDINE 50 grams of 2-(α-cyanobenzyl)-3-nitro-6-chloropyridine were dissolved in 200 ml. of acetone, 70 ml. of 30% aqueous hydrogen peroxide added and then with stirring there was gradually dropped a solution of 39 grams of KOH in 50 ml. of water with stirring. The solution heated by itself to 35° C. After 40 minutes there was no blue coloration upon dropwise adding further potassium hydroxide solution. The yellow-red solution was diluted with water and acidified with hydrochloric acid. The 2-benzoyl-3-nitro-6-hydroxypyridine crystallized out and was filtered off with suction after an hour and dried.

Yield: 40 grams; M.P. 103° to 105° C.

In the compounds thus obtained the nitro group in the three position was then reduced to the amino group, for example catalytically (with palladium, platinum or Raneynickel in alcohols, e.g., ethyl alcohol, dioxane or tetrahydrofuran at a temperature between 0° to 60° C. and 1 to 50 atmospheres absolute) or chemically with lithium aluminum hydride or aluminum-mercury-water in ether, dioxane or tetrahydrofuran between 0° and 60° C. If the compounds to be reduced contain sulfur it is recommended that the nitro group be hydrogenated, for example in dioxane or ethanol in the presence of Raneynickel or be reduced with titanium trichloride or tin (II) chloride.

The thus obtained 2-benzoyl-3-aminopyridine derivatives of the formula

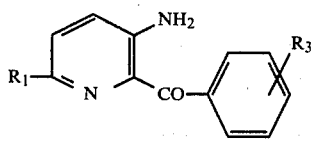
V (wherein $R_1$ and $R_3$ have the meanings given in connection with formula I) were then converted according to the process described in German Offenlegungsschrift No. 2,259,471 and related von Bebenburg U.S. application Ser No. 507,605 or German Offenlegungsschrift No. 2,419,386 or related von Bebenburg U.S. Pat. No. 3,941,775 into the corresponding 6-aza-1,2-dihydro-3H-1,4-benzodiazepine-(2) or the 4-N-oxide (substituted in the 7 position by the group $R_1$, in the 3 position by the group $R_2$ and in the phenyl nucleus by the group $R_3$) (formula II with V=OH, tautomeric form). In the thus obtained compounds the introduction of substituents in the 3 position can convert the products into compounds within V having different meanings. The conversion into the N-oxide and its deoxygenation likewise can be carried out. The processes employed to accomplish this can be those used in the above mentioned German Offenlegungsschrifts and the cited von Bebenburg U.S. application and von Bebenburg U.S. patent. The thus obtained 6-aza-1,2-dihydro-3H-1,4-benzo-diazepinone-(2) or its 4-N-oxide are then converted as follows into compounds of the formula

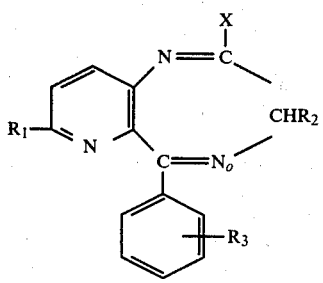
VI wherein $R_1$, $R_2$, $R_3$ have the already stated meanings, $N_0$ is N or N→O and X is the group —SH or the group —N(NO) alkyl (where Alkyl=a saturated alkyl group with 1 to 4 carbon atoms, e.g., methyl, ethyl, propyl, isopropyl, butyl or sec. butyl).

Compounds of formula V, wherein X is the group —SH are obtained for example by allowing the corresponding 6-aza-1,2-dihydro-3H-1,4-benzodiazepinone-(2) to react with phosphorus pentasulfide in an inert solvent such as benzene, toluene, dioxane, pyridine or chlorohydrocarbons, e.g., chloroform, at temperatures between 0° and 150° C. The thus obtained thiocompounds can then be further reacted in polar medium with alkyl amines (e.g., methyl amine, ethyl amine or butylamine) to the corresponding 2-alkylamino-6-aza-3H-1,4-benzodiazepines of formula VI wherein X is an alkylamino or butylamino). This reaction can be carried out in polar solvents such as lower alcohols (e.g., methanol or ethanol) or cycloalkanols (e.g., cyclohexanol) or excess amine at temperatures between 0° and 150° C.

Starting compounds of formula II wherein V is an alkoxy, alkylmercapto, benzylamino or dialkylamino group can be formed for example from compounds of formula II where V=OH, SH or $NH_2$ or their tautomeric form; if these are first converted into their alkali salt (e.g., sodium salt) and then alkylated or benzylated in conventional manner.

From those compounds of formula VI wherein X is an alkylamino group (or an alkylimino group) there can be obtained compounds of formula VI where X is the group —N(NO) alkyl by nitrosoation. This nitrosoation takes place by treating the corresponding 2-$C_1$ to $C_4$ alkylamino-5-phenyl-6-aza-3H-1,4-benzodiazepine with nitrous acid in the conventional way for nitrosoation of secondary amines. In detail such a nitrosoation can be carried out for example as follows:

26 grams of 2-methylamino-5-(o-chlorophenyl)-6-aza-7-chloro-3H,1,4-benzodiazepine-4-oxide were dissolved in 190 ml. of glacial acetic acid, then there were added in portions with stirring at 20° C. 8.5 grams of sodium nitrite. After 60 minutes of stirring the composition was diluted with 600 ml. of water, whereupon the reaction product, 2-(N-nitroso-methylamino)-5-(o-chlorophenyl)-6-aza-7-chloro-3H-1,4-benzodiazepine-4-oxide crystallized out. It was filtered off with suction and washed with water and a little ethanol. The reaction product was sufficiently pure to be used for the further reaction.

(Yield: 25 grams; M.P. 196° to 198° C.)

The abovementioned compounds of formula VI wherein X is an alkylamino group can also be obtained if there is reacted the corresponding 6-aza-1,2-dihydro-3H-1,4-benzodiazepine-(2) (in the tautomeric form compounds of formula VI where X=OH) with a $C_1$ to $C_4$ alkylamine (e.g., $CH_3NH_2$, $C_2H_5NH_2$, $C_3H_7NH_2$ and $C_4H_9NH_2$) with addition of titanium tetrachloride. For example there can be obtained 2-methylamino-5-(o-chlorophenyl)-6-aza-7-chloro-3H-1,4-benzodiazepine in the following manner.

A mixture of 6.1 grams of 5-(o-chlorophenyl)-6-aza-7-chloro-1,2-dihydro-3H-1,4-benzodiazepinone-(2) and 50 ml. of toluene were treated with 3.1 grams of methylamine and to this there was dropped in while coating with ice at 5° 15° C. 1,3 ml. of titanium tetrachloride. The mixture was stirred for 2 hours at 20° C., and then for an additional 3 hours at 90° C. After cooling the reaction product crystallized out. It was recrystallized from ethanol.

(Yield: 6 grams; M.P. 228° to 230° C.)

These compounds can then have the nitroso group introduced in the manner given previously.

There is obtained for example from compounds of formula VI wherein $R_1$, $R_2$, $R_3$ and $N_0$ have the stated meanings and X signifies the group —SH or the group —N(NO) alkyl where alkyl is a saturated alkyl group of 1 to 4 carbon atoms starting materials of formula II where V=—NH—NHR$_4$, if these compounds of formula VI are reacted with a hydrazine of the formula H$_2$N—NHR$_4$ VII where R$_4$ has the previously stated meanings. This reaction is carried out in polar solvents such as water, methanol, ethanol, dimethyl sulfoxide, dimethyl formamide, dioxane, pyridine, tertiary amines or mixtures of such materials or also in an excess of the hydrazine compound. The temperatures for example are between 0° and 150° C.

Another way for the production of compounds of formula II where V=—NH—NHR$_4$ comprises reacting under the same conditions as previously stated a compound of the formula:

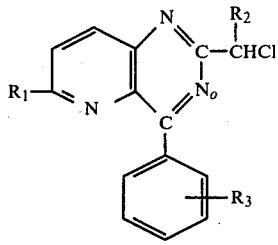

VIII wherein R$_1$, R$_2$, R$_3$ and N$_0$ have the stated meanings with a hydrazine H$_2$N—NHR$_4$ wherein R$_4$ has the given meaning.

There can also be employed a process wherein a compound of formula VIII is first reacted with a C$_1$ to C$_4$ alkylamine whereby a compound of formula VI is formed wherein R$_1$, R$_2$ and R$_3$ have the previously stated meanings and N$_0$ is the group $\geq$NO and X is a C$_1$ to C$_4$ alkylamino group, for example as illustrated below:

187 grams of 2-chloromethyl-4-(o-chlorophenyl)-5-aza-6-chloroquinazoline-3-oxide is introduced with stirring into a mixture of 1.6 liters of methanol and 300 grams of methylamine at room temperature. The nitroso compound goes into solution with development of gas. After some time the reaction product, 2-methylamino-5-(o-chlorophenyl)-6-aza-7-chloro-3H-1,4-benzodiazepine-4-oxide, begins to crystallize out. It is filtered off with suction. The compound is analytically pure.

(Yield: 159 grams; M.P. 242° to 244° C.)

The thus obtained 2-alkylamino-6-aza-3H-1,4-benzodiazepine-4-oxide can then, in a given case after previous deoxygenation of the nitrogen oxide group (described in more detail below), be nitrosoated in the manner previously described and then be reacted with the corresponding hydrazene compound. This reaction can take place for example analogous to the following directions.

There is introduced with stirring and cooling into a mixture of 150 ml. of hydrazene hydrate (100%) and 1000 ml. of methanol in portions within 30 minutes 107 grams of 2-(N-nitroso-methylamino)-5-(o-chloro-phenyl)-6-aza-7-chloro-3H-1,4-benzodiazepine-4-oxide. After a short time the reaction product, 2-hydrazino-5-(o-chlorophenyl)-6-aza-7-chloro-3H-1,4-benzodiazepine-4-oxide, begins to separate. Stirring is continued for 2 hours and then the product is filtered with suction. The material obtained is washed twice with methanol and then with some ether. It is sufficiently pure for further reactions.

Compounds of formula VIII can then be obtained in the following manner:

In a compound of formula V wherein R$_1$ and R$_3$ have the previously given meanings the amino group in the 3 position is acylated by a compound Hal—CO—CH$_2$R$_2$-Hal, where Hal is a chlorine or bromine atom, in a solvent, or suspension agent at temperatures between 20° and 150° C., in a given case in the presence of an acid binding agent. From the compound thus obtained there is then obtained by reaction with hydroxylamine in a polar agent (e.g., alcohols, dioxane or pyridine) at for example 20° to 100° C. a compound of the formula

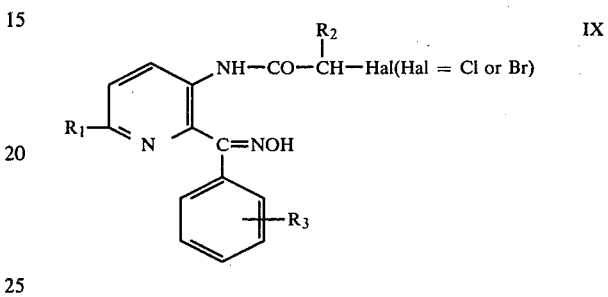

IX where R$_1$ R$_2$ and R$_3$ have the previously given meanings and Hal signifies chlorine or bromine. These compounds of formula IX are then cyclized with the splitting off of water. This water splitting reaction is carried out for example in polar solvents such as acetic acid, acetic anhydride, dimethyl sulfoxide, alcohols or also polyphosphoric acid, in a given case with addition of acid catalysts (for example hydrochloric acid, sulfuric acid or toluenesulfonic acid), preferably between 0° and 100° C. For example, the process can be carried out in the following manner:

185 grams of crude 2-(o-chlorobenzoyl-oximino)-3-chloroacetylamino-6-chloro-pyridine were dissolved with stirring at room temperature in 1000 ml. of concentrated sulfuric acid. The mixture is allowed to stand overnight and on the next morning is poured with stirring on 1 kg. of crushed ice. The slowly crystallizing 2-chloromethyl-4-(o-chlorophenyl)-5-aza-6-chloroquinazoline-3-oxide is filtered off with suction and washed well with water (yield: 110 grams). The compound is pure enough for further reaction. Thereis formed thereby compounds of formula VIII where N$_0$ is the group $\geq$NO. From this there can be obtained the corresponding compounds wherein N$_0$ is a nitrogen atom, for example by deoxygenating the N-oxide compound in conventional manner. This deoxygenation can take place for example analogous to the manner given in German Offenlegungsschrift No. 2,259,471 (page 15, example 14) and related von Bebenburg U.S. application Ser. No. 507,605, example 14 or German OS 2,419,386 (page 15) or related von Bebenburg U.S. Pat. No. 3,941,775, col. 10.

Furthermore, starting materials of formula II where V=—NH—NHR$_4$ can also be obtained from those materials of formula II in which V is the group —N-H—NH$_2$ and/or R$_2$ represents a hydroxy group, mercapto group or an amino group while the remaining symbols have the previously given meanings if there is reacted such a compound with a compound of the formula:

R$_4$X or R$_2$'X wherein X is chlorine, bromine, iodine or the group —COHal (Hal is chlorine or bromine) or the group —CO—OAlkyl and Alkyl is a lower alkyl group or the group —CO—OAr and Ar is benzyl or phenyl, which in a given case is substituted, or the group —CO—OAcyl and Acyl is an aliphatic acyl group with 2 to 6 carbon atoms or the group —CO—NHR' and R' is hydrogen, an acyl, especially the acetyl group, or a nitro group or the group $ArSO_2O—$, wherein Ar is an aromatic group, particularly a phenyl or naphthyl group, in a given case substituted by one or more alkyl groups, or the group $—O—(SO_2)_{178}$ or the group —CH=CO or —N=CO and $R_4$ has the previously (in formula I) given meanings (except hydrogen) and $R_2'$ is an acyl group with 2 to 6 carbon atoms or a $C_1$ to $C_6$ alkyl group and in a given case in the process of production one or more acyl groups is again split off.

These reactions are carried out for example in inert solvents or suspension agents such as dioxane, dimethyl formamide, dimethyl sulfoxide, benzene, toluene, alcohols, tetrahydrofuran, pyridine, sulfolane, N-methyl pyrrolidone, carbon tetrachloride, tertiary amines or acetone at temperatures between 0° and 200° C., preferably 0° to 100° C. It is understood that mixtures of such solvents can be used. In many cases water and glacial acetic acid are also suitable. In a given case the process is carried out in the presence of customary acid binding agents such as alkali carbonates, alkali hydroxides, alkali bicarbonates, tertiary amines (e.g., triethylamine, tributyl amine or dimethyl aniline) or pyridines.

The reaction can also be carried out via the corresponding alkali compounds. In such cases there is first produced the corresponding alkali compounds by means of alkali hydrides, alkali amides or alkali alcoholates (e.g., NaH, $NaNH_2$ or K-tert.butylate) at temperatures between 0° and 150° C. in an inert agent such as dioxane, dimethyl formamide, benzene, toluene or mixtures, for example toluene mixtures, e.g., a mixture of toluene and a little (0.1 to 0.5%) of dimethyl formamide. Then there is added the alkylating or acylating agent (particularly alkyl halides, e.g., methyl chloride, methyl bromide, methyl iodide, ethyl chloride or butyl chloride, acid halides, e.g., acetyl chloride, or dialkyl sulfates, e.g., dimethyl sulfate).

In a given case one or more of the acyl groups in the compounds thus obtained can be split off again, for example by saponification with dilute acids or by means of basic materials (e.g., potassium carbonate, sodium carbonate, aqueous alkali, alcoholic alkali solutions or $NH_3$) at room temperature or also by a brief boiling. As solvents or suspension agents there can be used for example water, lower aliphatic alcohols, cyclic ethers such as dioxane or tetrahydrofuran, aliphatic ethers, dimethyl formamide, etc., as well as mixture of these agents.

Those compounds of formula II wherein Y-Z is the group >C=N- can also be obtained from those compounds of formula II where Y-Z is the group >C=N(→O) by deoxygenation. This deoxygenation can take place by catalytic hydrogenation or by chemical deoxygenation. They can be carried out for example in solvents, such as dioxane, chloroform, aromatic hydrocarbons, dimethyl formamide, ethyl acetate, etc. As catalysts for the catalytic hydrogenation there are suited for example the conventional metallic hydrogenation catalysts, particularly noble metal catalysts (e.g., palladium-charcoal, platinum catalysts or Raney-nickel). As solvents for the hydrogenation there can also be used lower alcohols, e.g., ethyl alcohol. In a given case there can be used a pressure up to 50 atmospheres absolute. In the chemical deoxygenation there are preferably used titanium dichloride, phosphorus trichloride, phosphorous acid esters or dimethyl sulfoxide in the above mentioned solvents, especially dioxane, benzene or toluene. The temperatures at which the deoxygenation is carried out generally are between 0° and 200° C., preferably between 0° and 100° C.

Compounds of formula II wherein $R_1=H$ can be obtained for example from known 5-aryl-6-aza-1,2-dihydro-3H-1,4-benzodiazepinones-(2) (see Littell U.S. Pat. No. 3,314,941) if these compounds are reacted with a lower alkylamine (e.g., methylamine) and titanium tetrachloride, the 2-alkylamino-6-aza-5-phenyl-3H-1,4-benzodiazepine derivative obtained nitrosoated and subsequently reacted with a hydrazene of the formula $H_2N-NHR_4$ (the procedure is already described separately in the present specification).

Or one can also produce compounds of formula II where $R_1=H$ from known compounds of formula V where $R_1=H$ (Littell, U.S. Pat. No. 3,314,941) and these then converted into the hydraz ne of formula II in the manner already given for the compounds of formula V substituted by $R_1$.

Unless otherwise indicated all parts and percentages are by weight.

EXAMPLE 1a 6-(o-chlorophenyl)-8-chloro-4H-s-triazolo-(4,3-a)-pyrido-(2,3-f)-1,4-diazepine-5-oxide

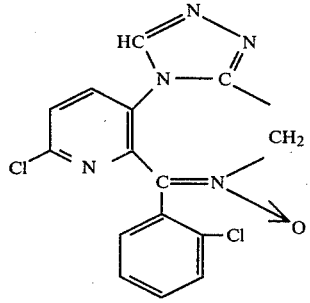

A mixture of 7 grams of 2-hydrazino-5-(o-chlorophenyl)-6-aza-7-chloro-3H-1,4-benzo diazepine-5-oxide, 100 ml. of ethanol, 0.5 grams of p-toluenesulfonic acid and 5 ml. of triethyl orthoformate were boiled at reflux for 30 minutes. The precipitated crystals after cooling were filtered oof with suction and washed with ethanol. They were analyzed as pure. Yield: 6.5 grams; M.P. 242°-244° C.

EXAMPLE 1b 6-phenyl-8-chloro-4H-s-triazolo-(4,3-a)-pyrido-(2,3-f)-(1,4)-diazepine-5-oxide (Formula as in Example 1a without the Cl attached to the phenyl group)

47 grams of 2-hydrazino-5-phenyl-6-aza-7-chloro-3H-1,4-benzodiazepine-4-oxide, 35 ml. of triethyl ortho formate and 2 grams of p-toluenesulfonic acid were heated in 400 ml. of ethanol for 1 hour under reflux. After cooling the product was filtered with suction and the reaction product was recrystallized from dimethyl-formamide-alcohol. M.P. 244°-246° C. (decomposition); Yield 40 grams.

EXAMPLE 1c 6-(o-chlorophenyl)-8-chloro-4H-s-triazolo-(4,3-a)-pyrido-(2,3-f)-(1,4)-diazepine (Formula as in Example 1a with =N— in place of =N→O)

A mixture of 5 grams of 2-hydrazino-5-(o-chlorophenyl)-6-aza-7-chloro-3H-benzo-1,4-diazepine, 80 ml. of ethanol, 0.5 grams of p-toluenesulfonic acid and 5 ml. of triethyl orthoformate were boiled at reflux for 1 hour. Upon cooling the reaction product crystallized out. It was filtered off and washed with ethanol and ether. M.P. 247°–248° C.; Yield 2 grams.

EXAMPLE 1d 6-phenyl-8-bromo-4H-s-triazolo-(4,3-a)-pyrido-(2,3-f)-(1,4)-diazepine

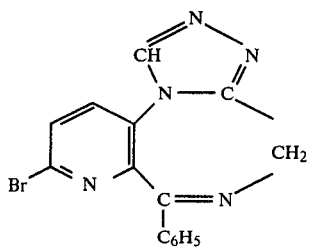

15 grams of 2-hydrazino-5-phenyl-6-aza-7-bromo-3H-1,4-benzodiazepine, 15 ml. of triethyl orthoformate and 0.3 grams of p-toluenesulfonic acid were heated in 150 ml. of ethanol for 0.5 hour at reflux. The solution was then filtered hot and the filtrate evaporated. The residue was recrystallized from methanol. M.P. 224°–226° C.; Yield 11 grams

EXAMPLE 2

1-keto-6-(o-chlorophenyl)-8-chloro-1,2-dihydro-4H-s-triazolo-(4,3-a)-pyrido-(2,3-f)-(1,4)-diazepine-5-oxide

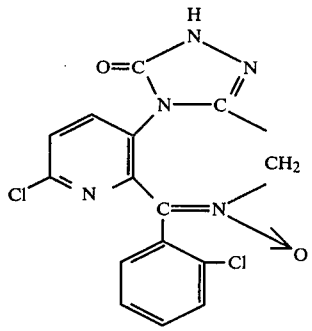

A mixture of 50 grams of 2-hydrazino-5-(o-chlorophenyl)-6-aza-7-chloro-3H-1,4-benzodiazepine-4-oxide, 400 ml. dioxane and 37 grams of N,N-carbonyldiimidazole were boiled for 45 minutes at reflux with stirring. The reaction product crystallized out upon cooling. There were added 500 ml. of ether, then the mixture filtered with suction, again stirred with 600 ml. of warm (40° C.) water and again filtered with suction. The product was pure enough for further reaction. It can be recrystallized from dimethyl formamide-ether, whereupon dimethyl formamide is included in the crystal lattice. The dimethyl formamide must then be removed by boiling with hexanol. Yield 41 grams; M.P. 200°–202° C.

EXAMPLE 3

1-keto-6-phenyl-8-chloro-1,2-dihydro-4H-s-triazolo-(4,3-a)-pyrido-(2,3-f)-(1,4)-diazepine-5-oxide

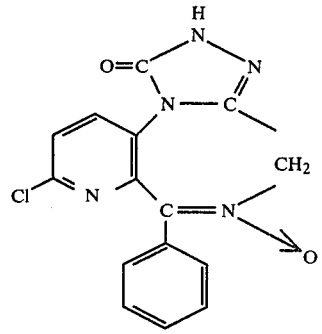

A mixture of 42 grams of 2-hydrazino-5-phenyl-6-aza-7-chloro-3H-1,4-benzodiazepine-4-oxide, 37 grams of N,N-carbonyldiimidazole and 300 ml. of dioxane were boiled for 45 minutes at reflux with stirring. Then the mixture was treated with 1 liter of water, whereupon the reaction product crystallized out. It was filtered off with suction, washed with water and methanol and again boiled with ethanolic HCl-solution. Yield 34 grams; M.P. 268°–270° C.

EXAMPLE 4a 1-ethoxy-6-(o-chloro-phenyl)-8-chloro-4H-s-triazolo-(4,3-a)-pyrido-(2,3-f)-(1,4)-diazepine

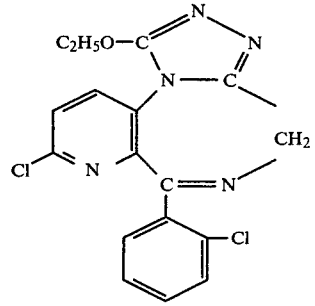

14 grams of 2-hydrazino-5-(o-chlorophenyl)-6-aza-7-chloro-3H-benzo-1,4-diazepine, 14 ml. of tetraethyl orthocarbonate and 150 ml. of ethanol were heated to 60° C. and there were added thereto a solution of 0.5 gram of p-toluenesulfonic acid in 20 ml. of ethanol. The mixture was then heated for 30 minutes under reflux, filered hot and allowed to cool. The reaction product was filtered off with suction and dissolved in hot methanol. After addition of water (15% of the amount of methanol) the mixture was treated with carbon and filtered. The reaction product crystallized out from the filtrate. M.P. 202°–204° C.; Yield 7.5 grams.

EXAMPLE 4b 1-bromomethyl-6-(o-chloro-phenyl)-8-chloro-4H-s-triazolo-(4,3-a)-pyrido-(2,3-f)-(1,4)-diazepine (Formula as in Example 4a with BrCH₂— in place of C₂H₅)— on the triazolo ring.)

16 grams of 2-hydrazino-5-(o-chlorophenyl)-6-aza-7-chloro-3H-benzo-1,4-diazepine, 24 grams of ethyl ortho bromoacetate and 0.5 grams of p-toluenesulfonic acid were heated in 100 ml. of ethanol for 20 minutes under reflux. After cooling the mixture was filtered, the filtrate evaporated and the residue dissolved in a little hot methanol. Upon cooling the reaction product crystallized out. M.P. 235°–240° C. (decomposition; beginning at 180° C. sintering and red coloration); Yield 3 grams.

EXAMPLE 4c 1-mercapto-6-(o-chloro-phenyl)-8-chloro-4H-s-triazolo-(4,3-a)-pyrido-(2,3-f)-1,4-diazepine (Formula as in Example 4a with HS— in place of $C_2H_5O$— on the triazolo ring)

35 grams of 2-hydrazino-5-(o-chlorophenyl)-6-aza-7-chloro-3H-benzo-1,4-diazepine, 100 ml. carbon disulfide, a solution of 30 grams of KOH in 70 ml. of water and 500 ml. of ethanol were heated under reflux for 2 hours, filtered, the reaction mixture evaporated and the residue dissolved in water. The product which crystallized out after acidification in glacial acetic acid was stirred with 200 ml. of methanol and warmed on the water bath (30 minutes). After cooling the crystalline product was filtered off with suction and washed with methanol. This product is a mixture of two isomers (M.P. 218°–220° C.). The above named 1-mercapto compound was obtained in pure form from this mixture by dissolving the product in hot dilute aqueous sodium hydroxide. Upon cooling the sodium salt of the 1-mercapto compound crystallized out. It was filtered off with suction, dissolved in warm water and acidified with glacial acetic acid. The separated crystals were filtered off with suction and washed with water. M.P. 250°–252° C.; Yield 12 grams

EXAMPLE 4d 6-phenyl-8-methylmercapto-4H-s-triazolo-(4,3-a)-pyrido-(2,3-f)-(1,4)-diazepine-5-oxide

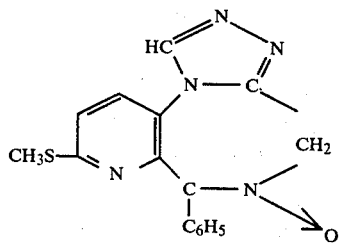

16 grams of 2-hydrazino-5-phenyl-6-aza-7-methylmercapto-3H-benzo-1,4-diazepine-4-oxide, 160 ml of ethanol, 11 ml of triethyl orthoformate and 0.3 grams of p-toluensulfonic acid were boiled at reflux for 30 minutes. The precipitated crystals were filtered after cooling and washed with ethanol and ether. Yield 14 grams. M.P. 244°–246° C. (decomposition).

EXAMPLE 5

6-(o-chloro-phenyl)-8-chloro-4H-tetrazolo-(4,5-a)-pyrido-(2,3-f)-(1,4)-diazepine

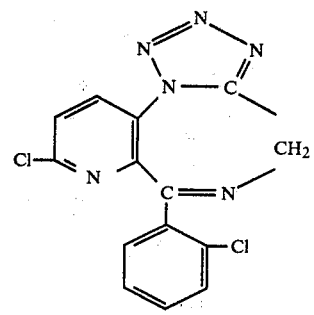

5 grams of 2-hydrazino-5-(o-chlorophenyl)-6-aza-7-chloro-3H-benzo-1,4-diazepine were stirred with 50 ml. of acetic acid (99%) and there were added thereto in portions at 20°–30° C. 3 grams of $NaNO_2$. Stirring was then carried out for another 30 minutes and the product treated with water. The reaction product crystallized out and was recrystallized from methanol. M.P. 200°–202° C.; Yield 1.5 grams.

EXAMPLE 6a 1-keto-2-methyl-6-(o-chloro-phenyl)-8-chloro-1,2-dihydro-4H-s-triazolo-(4,3-a)-pyrido)-(2,3-f)-(1,4)-diazepine-5-oxide

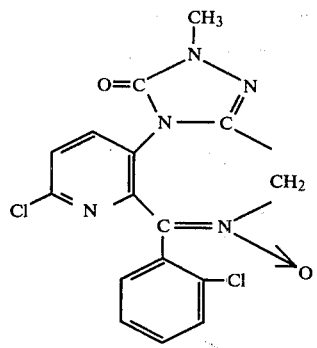

10 grams of 1-keto-6-(o-chloro-phenyl)-8-chloro-1,2-dihydro-4H-s-triazolo-(4,3-a)-pyrido-(2,3-f)-(1,4)-diazepine-5-oxide were stirred in 50 ml. of dimethyl formamide, than 20 ml. of 10% aqueous sodium hydroxide added and the slightly heated solution cooled to 20° C. Then there were added 5 grams of methyl iodide and stirring continued for 30 minutes during which the temperature increased to 30° C. The mixture was then heated to 40° C. and a further 10 grams of methyl iodide added. Thereupon there were added 400 ml. of water and after stirring for 1 hour the precipitated product was filtered off with suction. It was recrystallized from dimethyl formamide-ether. Yield 6 grams; M.P. 248°–250° C.

EXAMPLE 6b 1-methylmercapto-6-(o-chloro-phenyl)-8-chloro-4H-s-triazolo-(4,3-a)-pyrido-(2,3-f)-(1,4)-diazepine

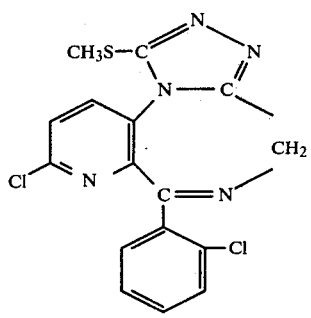

7 grams of 1-mercapto-6-(o-chloro-phenyl)-8-chloro-4H-s-triazolo-(4,3-a)-pyrido-(2,3-f)-(1,4)-diazepine were dissolved in 300 ml. of warm 5% aqueous sodium hydroxide. After cooling to 30° C. there were added 10 ml. of methyl iodide and stirring continued for one hour. The aqueous solution was decanted off from the separated oily reaction product and the residue stirred with ether, whereupon crystallization took place. Suction filtration was carried out and the product washed with ether. M.P. 230°-232° C.; Yield 6 grams.

EXAMPLE 6c 4-methoxy-6-(o-chloro-phenyl)-8-chloro-4H-s-triazolo-(4,3-a)-pyrido-(2,3-f)-(1,4)-diazepine

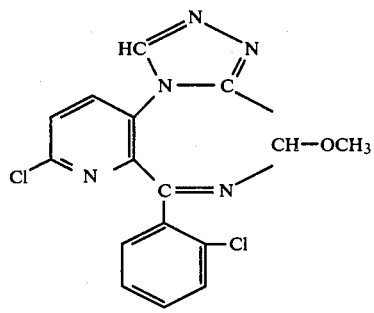

12 grams of 4-acetoxy-6-(o-chloro-phenyl)-8-chloro-4H-s-triazolo-(4,3-a)-pyrido-(2,3-f)-(1,4)-diazepine were stirred with 400 ml. of methanol and warmed to 40° C. whereupon the greatest portion dissolved. Then there were added 4 ml. of 10 N-alcoholic hydrochloric acid and heating carried out for 15 minutes under reflux. Upon cooling the reaction product crystallized out and was washed with methanol. M.P. 240°-243° C. (decomposition); Yield 8 grams.

EXAMPLE 6d 1-keto-2-cyanomethyl-6-(o-chlorophenyl)-8-chloro-1,2-dihydro-4H-s-triazolo-(4,3-a)-pyrido-(2,3-f)-(1,4)-diazepine

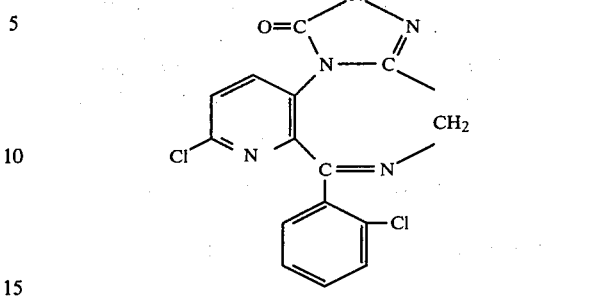

20 grams of 1-keto-6-(o-chlorophenyl)-8-chloro-1,3-dihydro-4H-s-triazolo-(4,3-a)-pyrido-(2,3-f)-(1,4)-diazepine were dissolved in 100 ml. of dimethyl formamide, 1.8 grams of sodium hydride (about 80%) added with cooling, further stirred for 5 minutes, then 5 grams of chloroacetonitrile added (the temperature increased from 30° C. to about 50° C.) and stirring continued for 30 minutes. Then it was poured into about 1 liter of water, shaken with chloroform, the chloroform phase washed with dilute aqueous sodium hydroxide and subsequently with water, dried, suction filtered over a silica gel layer and evaporated. The chloroform residue crystallized upon triturating with methanol and was recrystallized from methanol. M.P. 198°-200° C.; Yield 8 grams.

EXAMPLE 6e 1-keto-2-allyl-6-(o-chlorophenyl)-8-chloro-1,2-dihydro-4H-s-triazolo-(4,3-a)-pyrido-(2,3-f)-(1,4)-diazepine (Formula same as in Example 6d with —CH<sub>2</sub>—CH=CH<sub>2</sub> in place of —CH<sub>2</sub>—CN on the triazole ring)

The compound was produced analogous to Example 6d from 20 grams of 1-keto-6-(o-chlorophenyl)-8-chloro-1,2-dihydro-4H-s-triazolo-(4,3-a)-pyrido-(2,3-f)-(1,4)-diazepine and 8 grams of allyl bromide using 1.8 grams of NaH (about 8%) and 100 ml. of dimethyl formamide. The chloroform residue was recrystallized twice from methanol. M.P. 142°-144° C.; Yield 10 grams.

EXAMPLE 6f 1-keto-2-propargyl-6-(o-chlorophenyl)-8-chloro-1,2-dihydro-4H-s-triazolo-(4,3-a)-pyrido-(2,3-f)-(1,4)-diazepine Formula same as in Example 6d with —CH<sub>2</sub>—C≡CH in place of —CH<sub>2</sub>—CN on the triazole ring)

The compound was produced analogous to Example 6d from 20 grams of 1-keto-6-(o-chlorophenyl)-8-chloro-1,2-dihydro-4H-s-triazolo-(4,3-a)-pyrido-(2,3-f)-(1,4)-diazepine and 8 grams of propargyl bromide using 1.8 grams of NaH (about 80%) and 100 ml. of dimethyl formamide.

The chloroform residue was crystallized first from methanol and then from alcohol-gasoline. M.P. 160°-162° C.; Yield 9 grams.

EXAMPLE 6g 1-keto-2-methoxymethyl-6-(o-chlorophenyl)-8-chloro-1,2-dihydro-4H-s-triazolo-(4,3-a)-pyrido-(2,3-f)-(1,4)-diazepine (Formula as in Example 6d with —CH₂—O—CH₃ in place of —CH₂—CN on the triazole ring)

The process was analogous to Example 6d starting from 20 grams of 1-keto-6-(o-chlorophenyl)-8-chloro-1,2-dihydro-4H-s-triazolo-(4,3-a)-pyrido-(2,3-f)-(1,4)-diazepine and 6.5 ml. of chloromethyl-methylether using 1.8 grams of NaH (about 80%) and 100 ml. of dimethyl formamide.

The chloroform residue was dissolved in hot methanol. Crystallization took place upon inoculation. The product obtained was dissolved in hot ethanol for purification and acidified with ethanolic hydrochloric acid. Upon cooling the hydrochloride of the reaction product crystallized out (8 grams). This was dissolved in dimethyl sulfoxide at 20° C. and the solution treated with aqueous NH₃ up to the beginning of crystallization. Stirring was continued for one hour, filtered with suction and then washed with water. M.P. 180°-182° C.; Yield 7 grams.

EXAMPLE 6h 1-keto-2-acetonyl-6-(o-chlorophenyl)-8-chloro-1,2-dihydro-4H-s-triazolo-(4,3-a)-pyrido-(2,3-f)-(1,4)-diazepine (Formula as in Example 6d with —CH₂—CO—CH₃ in place of —CH₂—CN on the triazole ring)

The process was analogous to 6d starting from 20 grams of 1-keto-6-(o-chlorophenyl)-8-chloro-1,2-dihydro-4H-s-triazolo-(4,3-a)-pyrido-(2,3-f)-(1,4)-diazepine and 6.5 grams of chloroacetone using 1.8 grams of NaH (about 80%) and 100 ml. of dimethyl formamide. The chloroform residue (oil) was dissolved in about 50 ml. of hot methanol. Upon cooling an inoculation the reaction product crystallized out. M.P. 178°-180° C.; Yield 14 grams.

EXAMPLE 6i 1-keto-2-(β-dimethylaminoethyl)-6-(o-chlorophenyl)-8-chloro-1,2-dihydro-4H-s-triazolo-(4,3-a)-pyrido-(2,3-f)-(1,4)-diazepine (Formula as in Example 6d with —CH₂—CH₂N(CH₃)₂ in place of —CH₂—CN on the triazole ring)

15 grams of 1-keto-6-(o-chlorophenyl)-8-chloro-1,2-dihydro-4H-s-triazolo-(4,3-a)-pyrido-(2,3-f)-(1,4)-diazepine were stirred in 20 ml. of dimethyl formamide, then 3 grams of sodium methylate added, the mixture warmed with stirring to 60° C. and then 5 grams of β-dimethylaminoethyl chloride (base) added. Then the mixture was heated at 60°-70° C. for 30 minutes. Next there were again added 3 grams of sodium methylate and a further 5 grams of β-dimethylaminoethyl chloride (base) and the mixture warmed again for 30 minutes with stirring. The mixture was treated with water up to turbidity, whereupon the reaction product crystallized out. It was dissolved in a little methanol, ethanolic HCl solution added up to acid reaction and treated with ether up to turbidity. The hydrochloride then crystallized out. Yield 9 grams; M.P. of the hydrochloride 216°-218° C.

EXAMPLE 7

4-hydroxy-6-(o-chloro(or fluoro)phenyl)-8-chloro-4H-s-triazolo-(4,3-a)-pyrido-(2,3-f)-(1,4)-diazepine

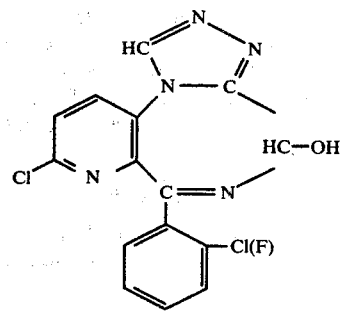

PREPARATION OF THE 6-(O-CHLOROPHENYL) COMPOUND 24 grams of 4-acetoxy-6-(o-chlorophenyl)-8-chloro-4H-s-triazolo-(4,3-a)-pyrido-(2,3-f)-(1,4)-diazepine were stirred with 60 ml. of n-propanol and there was added a mixture of 10 grams of powdered potassium hydroxide and 100 ml. of nOpropanol. The mixture was stirred for 15 minutes at room temperature. Then it was acidified with glacial acetic acid and 600 ml. of water added. The reaction product crystallized out. It was filtered off with suction then washed with water. The product can be recrystallized from dimethyl formamide-ether, whereby it is subsequently boiled with ethanol for 30 minutes to completely remove the dimethyl formamide. Yield 17 grams; M.P. 310° C.

PREPARATION OF THE 6-(O-FLUOROPHENYL) COMPOUND

In an analogous manner there was obtained the corresponding 6-(o-fluorophenyl) compound from 22 grams of 4-acetoxy-6-(o-fluorophenyl)-8-chloro-4H-s-triazolo-(4,3-a)-pyrido-(2,3-f)-1,4-diazepine in 100 ml. of propanol and a solution of 10 grams of KOH in 100 ml. of propanol. The reaction product was recrystallized from dimethyl formamide-ether. M.P. 290° C.; Yield 16 grams.

EXAMPLE 8

1-keto-4-hydroxy-6-(o-chlorophenyl)-8-chloro-1,2-dihydro-4H-s-triazolo-(4,3-a)-pyrido-(2,3-f)-(1,4)-diazepine

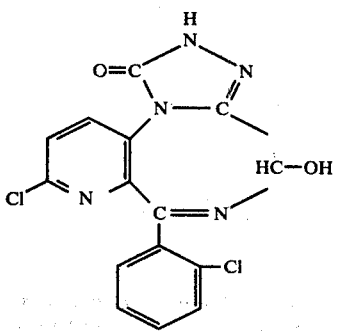

9 grams of 1-keto-4-acetoxy-6-(o-chlorophenyl)-8-chloro-1,2-dihydro-4H-s-triazolo-(4,3-a)-pyrido-(2,3-f)-(1,4)-diazepine were stirred with 60 ml. of n-propanol and a mixture of 10 grams of powdered potassium hydroxide and 100 ml. of n-propanol added. The mixture was stirred for 15 minutes at room temperature. Then it was acidified with glacial acetic acid and 600 ml. of water added. The reaction product crystallized out. It was filtered off with suction and then washed with water. The product can be recrystallized from dimethylformamide-ether whereupon it is subsequently boiled with ethanol for 30 minutes for the complete removal of the dimethyl formamide. Yield 5 grams; M.P. 260°–262° C.

EXAMPLE 9a 1-keto-6-(o-chlorophenyl)-8-pyrrolidino-1,2-dihydro-4H-s-triazolo-(4,3-a)-pyrido-(2,3-f)-(1,4)-diazepine-5-oxide

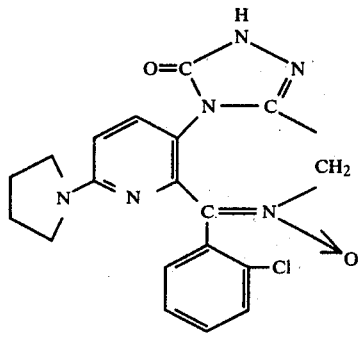

15 grams of 1-keto-6-(o-chlorophenyl)-8-chloro-1,2-dihydro-4H-s-triazolo-(4,3-a)-pyrido-(2,3-f)-(1,4)-diazepine-5-oxide in 50 ml. of pyrrolidine were boiled at reflux with stirring for 1 hour. Then it was poured into 600 ml. of water and neutralized with acetic acid. The precipitated material was shaken with chloroform, the chloroform layer washed with water, dried and evaporated to dryness. The residue was dissolved in methanol, acidified with ethanolic HCl solution and treated with ether up to the beginning of turbidity. The material crystallized out. It was filtered off with suction and washed with methanol-ether, and then recrystallized again from methanol-ether. Yield 4 grams; M.P. 200° C. (hydrochloride).

EXAMPLE 9b 1-keto-6-(o-chlorophenyl)-8-pyrrolidino-1,2-dihydro-4H-s-triazolo-(4,3-a)-pyrido-(2,3-f)-(1,4)-diazepine (Formula as in Example 9a with

in place of

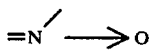

in the 7-ring)

20 grams of 1-keto-6-(o-chlorophenyl)-8-chloro-1,2-dihydro-4H-s-triazolo-(4,3-a)-pyrido-(2,3-f)-(1,4)-diazepine were boiled with 60 ml. of pyrrolidine for 1 hour under reflux. Then the mixture was poured into 1 liter of water and acidified with glacial acetic acid whereupon the reaction product crystallized out. This was dissolved in alcohol, the alcoholic solution concentrated to about 70 ml. and ether added. The crystallized material was recrystallized from methanol. M.P. 228°–230° C.; Yield 8 grams.

EXAMPLE 10a 1-keto-6-(o-chlorophenyl)-8-dimethylamino-1,2-dihydro-4H-s-triazolo-(4,3-a)-pyrido-(2,3-f)-(1,4)-diazepine

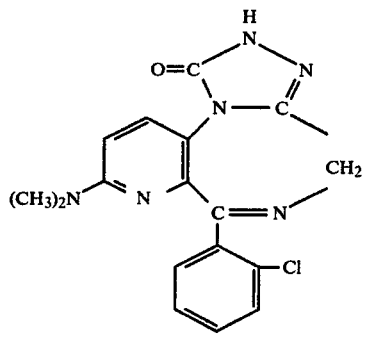

A mixture of 19 grams of 1-keto-6-(o-chlorophenyl)-8-chloro-1,2-dihydro-4H-s-triazolo-(4,3-a)-pyrido-(2,3-f)-(1,4)-diazepine, 80 grams of dimethylamine and 500 ml. of ethanol were heated in the autoclave for 8 hours at 100°–110° C. The solution was evaporated to dryness, the residue stirred with water, filtered off with suction and washed several times with water. Then it was recrystallized from methanol. Yield 8 grams; M.P. 244°–246° C.

EXAMPLE 10b 6-(o-chloro-phenyl)-8-dimethylamino-4H-s-triazolo-(4,3-a)-pyrido-(2,3-f)-(1,4)-diazepine (Formula as in Example 10a with —CH=N— in place of —CO—NH— in the 5-ring)

This compound was obtained in an analogous manner to that given in Example 10a from 15 grams of 6-(o-chloro-phenyl)-8-chloro-4H-s-triazolo-(4,3-a)-pyrido-(2,3-f)-(1,4)-diazepine and 55 grams of dimethylamine in 500 ml. of ethanol by heating for 5 hours at 120° C. M.P. 240°–242° C. (from methanol); Yield 8.5 grams.

EXAMPLE 11a 6-(o-chlorophenyl)-8-chloro-4H-s-triazolo-(4,3-a)-pyrido-(2,3-f)-(1,4)-diazepine (by deoxygenation of the N-oxide)

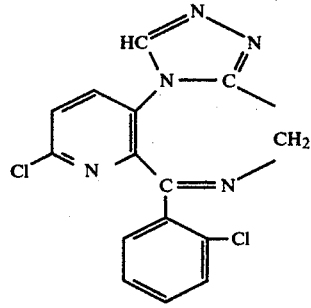

11 grams of 6-(o-chlorophenyl)-8-chloro-4H-s-triazolo-(4,3-a)-pyrido-(2,3-f)-(1,4)-diazepine-4-oxide were boiled at reflux in a mixture of 200 ml. of dioxane and 30 ml. phosphorus trichloride for 3 hours. The mixture was evaporated in a vacuum, the residue taken up in chloroform and dilute aqueous sodium hydroxide, the chloroform layer washed with water, dried, evaporated and the residue dissolved in methanol, whereby it crystallized. The product filtered off with suction was recrystallized from hexanol. Yield 8 grams; M.P. 247°–248° C.

EXAMPLE 11b 6-(o-fluorophenyl)-8-chloro-4H-s-triazolo-(4,3-a)-pyrido-(2,3-f)-(1,4)-diazepine (Formula as in Example 11a with F in place of Cl in the phenyl ring)

25 grams of 6-(o-fluorophenyl)-8-chloro-4H-s-triazolo-(4,3-a)-pyrido-(2,3-f)-(1,4)-diazepine-5-oxide were stirred with 300 ml. of dioxane, 20 ml. of PCl$_3$ dropped in at 40° C. and the mixture heated one hour under reflux. After cooling the reaction product (HCl salt) filtered off with suction was dissolved in methanol. Upon treating with aqueous NH$_3$ the base crystallized out and was recrystallized from methanol and carbon. M.P. 198°–200° C.; Yield 7.5 grams.

EXAMPLE 11c 6-phenyl-8-chloro-4H-s-triazolo-(4,3-a)-pyrido-(2,3-f)-(1,4)-diazepine (Formula as in Example 11a without Cl in the phenyl ring)

The process was analogous to Example 11b using 25 grams of 6-phenyl-8-chloro-4H-s-triazolo-(4,3-a)-pyrido-(2,3-f)-(1,4)-diazepine-5-oxide and 20 ml. PCl$_3$ in 300 ml. of dioxane. After cooling the reaction mixture was made alkaline, the dioxane phase separated, concentrated and the residue stirred with methanol, whereupon crystallization took place. It was recrystallized from methanol and carbon. M.P. 180°–182° C.; Yield 5.6 grams.

EXAMPLE 11d 6-(o-chloro-phenyl)-8-chloro-5,6-dihydro-4H-s-triazolo-(4,3-a)-pyrido-(2,3-f)-(1,4)-diazepine

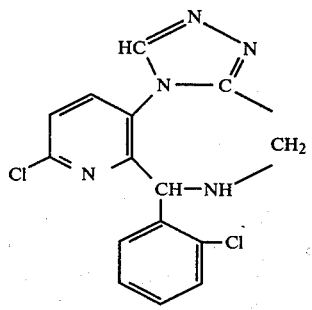

29 grams of 6-(o-chloro-phenyl)-8-chloro-4H-s-triazolo-(4,3-a)-pyrido-(2,3-f)-(1,4)-diazepine were hydrogenated in 500 ml. of dimethyl formamide in the presence of 20 grams of Raney-nickel at 50 atmospheres absolute at 60°–70° C. The filtrate was evaporated, the residue stirred with water and shaken with chloroform. The chloroform residue was stirred with methanol and the thus obtained crystalline reaction product first crystallized from dioxane-gasoline and then recrystallized from methyl ethyl ketone-gasoline. M.P. 206°–208° C.; Yield 10 grams.

EXAMPLE 11e 6-phenyl-8-methylmercapto-4H-s-triazolo-(4,3-a)-pyrido-(2,3-f)-(1,4)-diazepine

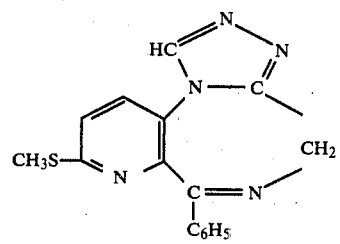

The compound was produced analogous to Example 11c from 13 grams of 6-phenyl-8-methylmercapto-4H-s-triazolo-(4,3-a)-pyrido-(2,3-f)-(1,4)-diazepine-5-oxide and 10 ml PCl$_3$ in 200 ml of dioxane. The reaction product was recrystallined from methanol and carbon. Yield 5 grams M.P. 190°–192° C.

EXAMPLE 12

1-keto-6-(o-chlorophenyl)-8-chloro-1,2-dihydro-4H-s-triazolo-(4,3-a)-pyrido-(2,3-f)-(1,4)-diazepine

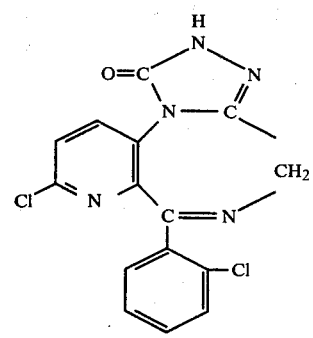

33 grams of 1-keto-6-(o-chlorophenyl)-8-chloro-1,2-dihydro-4H-s-triazolo-(4,3-a)-pyrido-(2,3-f)-(1,4)-diazepine-5-oxide were hydrogenated in 450 ml. of dimethyl formamide with the addition of 15 grams of Raney-nickel at 60° to 70° C. and 50 atmospheres absolute. After filtering off the catalyst with suction, the filtrate was concentrated to 100 ml. and then treated with water to the point of turbidity whereupon the desired reaction product crystallized out. It was recrystallized from alcohol and then also from ethyl acetate-gasoline. Yield 8 grams; M.P. 222°–224° C.

The dimethyl formamide mother liquor contained a great amount of 1-keto-6-(o-chlorophenyl)-8-chloro-1,2,5,6-tetrahydro-4H-s-triazolo-(4,3-a)-pyrido-(2,3-f)-1,4-diazepine, which can be obtained through further addition of water and then through several recrystallizations from methanol (formula as in Example 11d with the group —CO—NH— in place of —CH=N— in the triazole ring). Yield 3.5 grams; M.P. 180°–182° C.

EXAMPLE 13

1-keto-2-methyl-6-(o-chlorophenyl)-8-chloro-1,2-dihydro-4H-s-triazolo-(4,3-a)-pyrido-(2,3-f)-(1,4)-diazepine

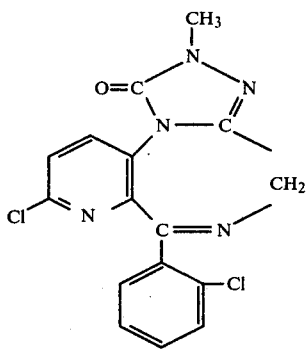

33 grams of 1-keto-6-phenyl-8-chloro-1,2-dihydro-4H-s-triazolo-(4,3-a)-pyrido-(2,3-f)-(1,4)-diazepine-5-oxide were stirred with 330 ml. of chloroform. Then there were dropped in 35 ml. of phosphorus trichloride and then the mixture was boiled at reflux for 4 hours with stirring. After cooling the solution was shaken twice with ice water and subsequently twice with 5% aqueous sodium hydroxide. The chloroform layer was dried with sodium sulfate and evaporated to dryness. The residue was recrystallized from dioxane-ether. Yield 10.5 grams; M.P. 200°–202° C.

EXAMPLE 14

1-keto-6-phenyl-8-chloro-1,2-dihydro-4H-s-triazolo-(4,3-a)-pyrido-(2,3-f)-(1,4)-diazepine

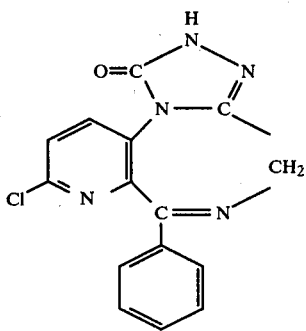

33 grams of 1-keto-6-phenyl-8-chloro-1,2-dihydro-4H-s-triazolo-(4,3-a)-pyrido-(2,3-f)-(1,4)-diazepine-5-oxide were hydrogenated with 15 grams of Raney-nickel in 450 ml. of dimethyl formamide at 50 atmospheres absolute and 60°–70° C. After filtering off the catalyst with suction, the solution was concentrated to 100 ml., and then treated with water up to turbidity, whereupon the reaction product crystallized out. It was recrystallized from ethanol several times. Yield 15 grams; M.P. 222°–224° C.

EXAMPLE 15

6-(o-chloro-phenyl)-8-chloro-5-hydroxy-5,6-dihydro-4H-s-triazolo-(4,3-a)-pyrido-(2,3-f)-(1,4)-diazepine

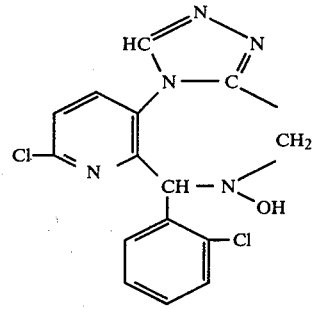

17 grams of 6-(o-chloro-phenyl)-8-chloro-4H-s-triazolo-(4,3-a)-pyrido-(2,3-f)-(1,4)-diazepine-5-oxide were stirred with 100 ml. of methanol, then 3.5 grams of sodium cyano boronate (NaBH$_3$CN) were added and a pH of 3–4 established by dropping in alcoholic HCl. After 1 hour there were again added 3.5 grams of NaBH$_3$CN. Stirring was continued for 2 hours and the product freed from undissolved starting material by filtering with suction. The product crystallized out of the filtrate after addition of water and ammonia was thoroughly stirred with warm ether. The product was filtered, the ether evaporated and the residue recrystallized from n-propanol. M.P. 230°–232° C.; Yield 2 grams.

EXAMPLE 16a 4-acetoxy-6-(o-chlorophenyl)-8-chloro-4H-s-triazolo-(4,3-a)-pyrido-(2,3-f)-(1,4)-diazepine

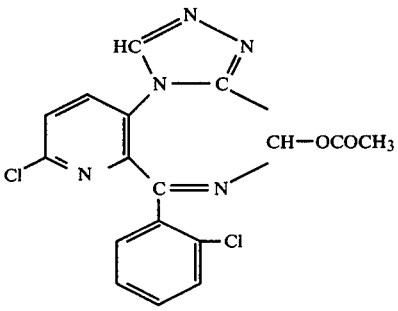

12 grams of 6-(o-chlorophenyl)-8-chloro-4H-s-triazolo-(4,3a)-pyrido-(2,3-f)-(1,4)-diazepine-5-oxide were boiled with stirring at reflux in 100 ml. of acetic anhydride for 1 hour. The reaction product crystallized out upon cooling. It was filtered off with suction and washed with glacial acetic acid and ether. It can be recrystallized from ethanol. Yield 8 grams; M.P. 230°–235° C.

EXAMPLE 16b 4-acetoxy-6-(o-fluorophenyl)-8-chloro-4H-s-triazolo-(4,3-a)-pyrido-(2,3-f)-(1,4)-diazepine (Formula as in Example 16a with F in place of Cl on the phenyl ring)

12 grams of 6-(o-fluorophenyl)-8-chloro-4H-s-triazolo-(4,3-a)-pyrido-(2,3-f)-(1,4)-diazepine-5-oxide were heated under reflux in 100 ml. of acetic anhydride. Then the mixture was evaporated, the residue dissolved in hot methanol and the product which crystallized out was recrystallized from methanol. M.P. 210°–212° C.; Yield 4 grams.

EXAMPLE 17

1-keto-4-acetoxy-6-(o-chlorophenyl)-8-chloro-1,2-dihydro-4H-s-triazolo-(4,3-a)-pyrido-(2,3-f)-(1,4)-diazepine

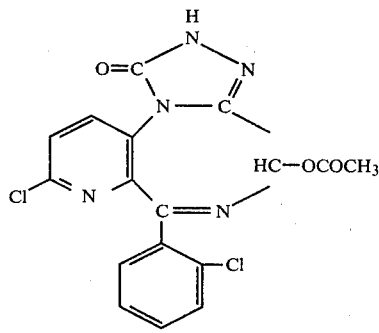

10 grams of 1-keto-2-methyl-6-(o-chlorophenyl)-8-chloro-1,2-dihydro-4H-s-triazolo-(4,3-a)-pyrido-(2,3-f)-(1,4)-diazepine-5-oxide were boiled in a mixture of 20 ml. of glacial acetic and 20 ml. of acetic anhydride for 30 minutes with stirring. After cooling the mixture was evaporated in a vacuum and the residue dissolved in hot methanol. The reaction product crystallized out upon cooling. It was filtered off with suction and washed with methanol. Yield 9 grams; M.P. 232°–236° C.

The compounds of the invention are suited for the production of pharmaceutical compositions and preparations. The pharmaceutical compositions or drugs contain as the active material one or several of the compounds of the invention, in a given case in admixture with other pharmacologically or pharmaceutically effective materials. The production of the medicine can take place in known manner and there can be used known and customary pharmaceutical assistants, carriers and diluents.

Such carriers and assistants as set forth for example are those recommended in the following literature as adjuvants for pharmacy, cosmetic and related fields such as Ullmann's *Encyklopadie der technischer Chemie,* Vol. 4 (1953), pages 1 to 39; *Journal of Pharmaceutical Sciences,* Vol. 52 (1963), pages 918 et seq.; H. v. Czetsch-Lindenwald, *Hilfstoffe fur Pharmazie und angrenzende Gebiete;* Pharm. Ind. Vol. 2 (1961), pages 72 et seq.; Dr. H. P. Fiedler, *Lexicon der Hilfstoffe fur Pharmazie, Kosmetik und angrenzende Gebiete,* Cantor Kg. Aulendorf 1. Wurtt, 1971.

Examples of such materials include gelatin, natural sugars such as sucrose or lactose, lecithin, pectin, starch (for example corn starch), alginic acids, tylose, talc, lycopodium, silica (for example colloidal silica), glucose, cellulose, cellulose derivatives for example cellulose ethers in which the cellulose hydroxyl groups are partially etherified with lower aliphatic alcohols and/or lower saturated oxyalcohols (for example, methyl hydroxypropyl cellulose, methyl cellulose, hydroxyethyl cellulose), stearates, e.g., methylstearate, and glyceryl stearate, magnesium and calcium salts of fatty acids with 12 to 22 carbon atoms, especially saturated acids (for example calcium stearate, calcium laurate, magnesium oleate, calcium palmitate, calcium behenate and magnesium stearate), emulsifiers, oils and fats, especially of plant origin (for example, peanut oil, castor oil, olive oil, sesame oil, cottonseed oil, corn oil, wheat germ oil, sunflower seed oil, cod-liver oil, mono-, di- and triglycerides of saturated fatty acids ($C_{12}H_{24}O_2$ to $C_{18}H_{36}O_2$ and their mixtures, e.g., glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol dipropylene glycol, polyethylene glycol 400 and other polyethylene glycols, as well as derivatives of such alcohols and polyglycols, esters of saturated and unsaturated fatty acids (2 to 22 carbon atoms, especially 10 to 18 carbon atoms), with mono- (1 to 20 carbon atoms alkanols) or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, monoacetin, triacetin, glyceryl oleate, ethylene glycol stearate; such esters of polyvalent alcohols can in a given case also be etherified, benzyl benzoate, dioxolane, glycerine formal, glycol furfural, dimethyl acetamide, lactamide, lactates, e.g., ethyl lactate, ethyl carbonate, silicones (especially middle viscosity dimethyl polysiloxane), magnesium carbonate and the like.

For the production of solutions there can be used water or physiologically compatible organic solvents, as for example, ethanol, 1,2-propylene glycol, polyglycols, e.g., diethylene glycol, triethylene glycol and dipropylene glycol and their derivatives, dimethyl sulfoxide, fatty alcohols, e.g., stearyl alcohol, cetyl alcohol, lauryl alcohol and oleyl alcohol, triglycerides, e.g., glyceryl acetate, partial esters of glycerine, e.g., monoacetin, diacetin, glyceryl monostearate, glyceryl distearate, glyceryl monopalmitate, paraffins and the like.

In the production of the preparation there can be used known and conventional solvent aids, for example, emulsifiers. As solvent aids and emulsifiers there can be used for example polyvinyl pyrrolidone, sorbitan trioleate, lecithin, gum acacia, gum tragacanth, polyoxyethylated oleo triglycerides, linolized oleotriglycerides, polyoxyethylated sorbitan monooleate, polyoxyethylated fats, polyethylene oxide condensation products of fatty alcohols, alkyl phenols or fatty acids.

Polyoxyethylated means that the materials in question contain polyoxyethylene chains whose degree of polymerization is generally between 2 and 40 and especially between 10 and 20. Such materials can be obtained for example by reaction of the corresponding glyceride with ethylene oxide (for example 40 moles of ethylene oxide per mole of glyceride).

Example of oleotriglycerides are olive oil, peanut oil, castor oil, sesame oil, cottonseed oil, corn oil (see also Dr. H. P. Fiedler, *Lexicon der Hilfsstoffe fur Pharmazie, Kosmetik und augreuzende Gebiete* (1971), pages 191 to 195).

Furthermore, there can be added preservatives, stabilizers, buffers, for example calcium hydrogen phosphate, colloidal aluminum hydroxide, taste correctives, antioxidants and complex formers (for example ethylenediamine tetraacetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used for example sodium meta bisulfite, ascorbic acid, gallic acid, alkyl gallates, e.g., methyl gallate and ethyl gallate, butyl hydroxyanisole, nordihydrognaiaretic acid, tocopherols such as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxybenzoic acid esters (for example lower alkyl esters such as the methyl ester and the ethyl ester benzoic acid), sodium benzoate, trichloroisobutyl alcohol, phenol, cresol, benzethonium chloride and formalin derivatives.

The pharmacological and galenical treatment of the compounds of the invention take place according to the usual standard methods. For example, the active material of materials and assistants or carriers are well mixed by stirring or homogenization (for example by means of a colloid mill or ball mill), wherein the operation is generally carried out at temperatures between 20° and 80° C., preferably 20° to 50° C.

The application of the active materials or drugs can take place on the skin or mucous membrane or internally (parenterally), for example orally, enterally, pulmonally, rectally, nasally, vaginally, lingually, intravenously, intracardially, intramuscularly, intraperitoneally, intracutaneously or subcutaneously.

Other medicines can also be added.

The compounds of the invention for example in the tests of Cardiazol-shock (using the method of F. M. Berger et al., *J. Pharmacol. Exper. Therap.* Vol. 116 (1956), pages 337–342) show a good anticonvulsive action while at the same time disturbing side effects such as ataxia (tested on the rotating rod) and sedation (Evipan sleep test, *Arzneimittelforschung* Vol. 16 (1966), pages 901–910) are either practically absent or weak.

Such an anticonvulsive effect is obtained for example in above-mentioned test procedures at a dosage of 2 mg/kg. of body weight in mice. The anticonvulsive activity measurable in the animal experiments corresponds in people to an anxiolytic activity (anxiety releasing, anxiety lowering). This anxiolytic activity is comparable to the activity of the known medicine Diazepam.

The compounds of the invention are particularly distinguished by the fact that the main activity is not accompanied by disturbing side effects.

The lowest effective dosage in the above-mentioned animal experiments for example is:
0.1 mg./kg.: orally
0.1 mg./kg.: sublingually
0.05 mg./kg.: intravenously As a general dosage range, these can be used, for example:
0.1–2 mg./kg. orally, particularly 0.5–1 mg./kg.
0.1–2 mg./kg. sublingually, particularly 0.5–1 mg./kg.
0.05–0.3 mg./kg. intravenously, particularly 0.07–0.1 mg./kg.

The compounds of the invention are useful in treating neuroses, anxiety and stress conditions, neurovegetative disturbances, convulsion conditions, spasms of the skeletal muscle, abortus immineus and epilepsy. Furthermore, they can be employed for example in drug withdrawal cures and in assisting birth.

The pharmaceutical preparations generally contain between 0.1 and 0.5% of the active component (or components) of the invention.

The compounds can be delivered in the form of tablets, capsules, pills, dragees, suppositories, salves, gels, creams, powders, liquids, dusts or aerosols. As liquids there can be used oily or alcoholic or aqueous solutions or suspensions or emulsions. The preferred forms of use are as tablets which contain between 0.5 and 5 mg. of active material or solutions which contain between 0.01 and 0.1% of active material.

In individual doses the amount of active component of the invention can be used for example in an amount of:
 a. in oral dispensation between 0.5 and 2 mg.;
 b. in parenteral dispensation (for example, intravenously, intramuscularly) between 0.1 and 0.5 mg.; and,
 c. in rectal or vaginal dispensation between 0.5 and 2 mg.

(The dosages in each case are based on the free base.)

For example, there is recommended the use of 1 to 3 tablets containing 0.5 to 2 mg. of active ingredient 3 times daily or for example intravenously the injection 1 to 3 times daily of a 1 to 2 ml. ampoule containing 0.01 to 0.1 mg. of active substance. In oral preparations the minimum daily dosage for example is 0.05 mg.; the maximum daily dosage should not be over 20 mg.

In the treatment of dogs and cats the oral individual dosage in generaly is between 0.1 and 2 mg./kg/body weight; the parenteral individual dosage is between about 0.01 to 0.1 mg./kg/body weight. In the treatment of horses and cattle, the individual dosage orally is generally between 0.1 and 2 mg./kg.; the parenteral individual dosage is between 0.01 and 0.1 mg./kg. body weight.

The acute toxicity of the compounds of the invention in the mouse (expressed by the $LD_{50}$ mg./kg. method of Miller and Tainter, *Proc. Soc. Exper. Biol. and Med.*, Vol. 57 (1944), pages 261, et seq.) in oral application is between 500 mg./kg. and 8,000 mg./kg. (or above).

The drugs can be used in human medicine, in veterinary medicine, e.g., to treat cats, dogs, horses, sheep, cattle, goats and pigs or in agriculture. The drugs can be used alone or in admixture with other pharmacologically active materials.

What is claimed is:

1. A 6-phenyl-s-triazolo-(4,3-a)-pyrido-(2,3-f)-(1,4)-diazepine compound of the formula:

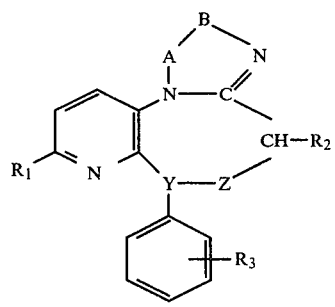

wherein $R_1$ is hydrogen or a halogen atom,
  $R_2$ is hydrogen or an alkyl group with 1 to 4 carbon atoms,
  $R_3$ is hydrogen, or a halogen
  the structural part A-B is the group, —CH=N—,
  and Y-Z is the group >C=N— or >C=N(→O), their optical isomers and their pharmaceutically acceptable salts.

2. A compound according to claim 1 wherein any halogen atom present has an atomic weight of 9 to 80.

3. A compound according to claim 1 wherein Y—Z is >C=N—.

4. A compound according to claim 3 wherein $R_1$ is chlorine, bromine or fluorine, $R_2$ is hydrogen and $R_3$ is hydrogen or chlorine.

5. A compound according to claim 4 wherein $R_1$ is chlorine, bromine or fluorine.

6. A compound according to claim 4 where $R_1$ is chlorine and $R_3$ is chlorine.

7. A compound according to claim 6 which is 6-(o-chlorophenyl)-8-chloro-4H-s-triazolo-(4,3-a)-pyrido-(2,3-f)-(1,4)-diazepine.

8. A compound according to claim 1 which is 6-(o-chlorophenyl)-8-chloro-4H-s-triazolo-(4,3-a)-pyrido-(2,3-f-)-(1,4)-diazepine 5-oxide.

9. A compound according to claim 1 which is 6-phenyl-8-bromo-4H-s-triazolo-(4,3-a)-pyrido-(2,3-f)-(1,4)-diazepine.

10. A compound according to claim 1 which is 6-(o-fluorophenyl)-8-chloro-4H-s-triazolo-(4,3-a)-pyrido-(2,3-f)-(1,4)-diazepine.

11. A compound according to claim 1 which is 6-phenyl-8-chloro-4H-s-triazolo-(4,3-a)-pyrido-(2,3-f)-(1,4)-diazepine.

12. A composition having stress relieving activity comprising an effective amount for such activity of a compound of claim 1 in a pharmaceutically acceptable carrier.

13. A method of relieving stress in a mammal comprising administering to the mammal an amount of the compounds of claim 1 sufficient to relieve stress.

14. A method according to claim 13 wherein the compound is administered orally.

15. A method according to claim 13 wherein the compound is administered intravenously.

16. A method according to claim 13 wherein the compound is administered sublingually.

* * * * *